(12) United States Patent
Craig et al.

(10) Patent No.: US 11,077,441 B2
(45) Date of Patent: Aug. 3, 2021

(54) METHODS FOR PROCESSING DROPLETS CONTAINING BIOLOGICAL ENTITIES

(71) Applicant: SPHERE FLUIDICS LIMITED, Babraham (GB)

(72) Inventors: Frank F. Craig, Babraham Cambridge (GB); Marian Rehak, Babraham Cambridge (GB); David Holmes, Babraham Cambridge (GB); Clive A. Smith, Babraham Cambridge (GB); Xin Liu, Babraham Cambridge (GB); Giuseppe Benazzi, Babraham Cambridge (GB); Xin Li, Babraham Cambridge (GB); Vinayaka Pawate, Babraham Cambridge (GB); Robert Frank Marchington, Cambridge (GB); Richard Francis Day, Great Cambourne (GB); Michael Stuart Hazell, Cambridge (GB)

(73) Assignee: Sphere Fluidics Limited, Cambridge (GB)

( * ) Notice: Subject to any disclaimer, the term of this patent is extended or adjusted under 35 U.S.C. 154(b) by 405 days.

(21) Appl. No.: 15/578,455

(22) PCT Filed: Jun. 3, 2016

(86) PCT No.: PCT/GB2016/051654
§ 371 (c)(1),
(2) Date: Nov. 30, 2017

(87) PCT Pub. No.: WO2016/193758
PCT Pub. Date: Dec. 8, 2016

(65) Prior Publication Data
US 2018/0133715 A1    May 17, 2018

(30) Foreign Application Priority Data
Jun. 3, 2015    (GB) .................................. 1509640

(51) Int. Cl.
*B01L 3/00* (2006.01)
*G01N 35/08* (2006.01)
(Continued)

(52) U.S. Cl.
CPC ... *B01L 3/502784* (2013.01); *B01L 3/502761* (2013.01); *C12M 47/04* (2013.01);
(Continued)

(58) Field of Classification Search
None
See application file for complete search history.

(56) References Cited

U.S. PATENT DOCUMENTS

2003/0015425 A1* 1/2003 Bohm ............. G01N 27/44743
204/453
2005/0221339 A1* 10/2005 Griffiths ............. G01N 33/5008
435/6.11

(Continued)

FOREIGN PATENT DOCUMENTS

WO    2007133710 A2    11/2007
WO    WO-2007133710 A2 * 11/2007 ............ B01F 3/0807
(Continued)

OTHER PUBLICATIONS

English Language Translation and Japanese Office Action; Notice of Reasons for Rejection; Application No. 2017-563104; dated Jun. 1, 2020; 11 Pgs.
(Continued)

*Primary Examiner* — Nghi V Nguyen
(74) *Attorney, Agent, or Firm* — Renner, Kenner, Greive, Bobak, Taylor & Weber

(57) ABSTRACT

Instruments and cartridges for processing droplets in emulsions containing biological entities such as cells. A method of such processing comprises providing a plurality of the entities in a fluid; preparing a droplet from the fluid; deter-
(Continued)

mining whether the droplet contains one or more entities of said plurality of entities, or whether said droplet does not contain a said entity; sorting said droplet dependent on an outcome of the determination; and dispensing the sorted droplet into a reservoir. The dispensing may comprise identifying and extracting the sorted droplet from a first fluidic flow path of said fluid by transferring the sorted droplet from into a second fluidic flow path and then ejecting the sorted droplet into a reservoir by applying pressure to the second fluidic flow path. The droplet contents may be tracked so that the contents of an individual droplet can be sorted, selectively dispensed, and retrieved.

19 Claims, 26 Drawing Sheets

(51) Int. Cl.
 *G01N 15/14* (2006.01)
 *C12M 1/00* (2006.01)
(52) U.S. Cl.
 CPC ......... *G01N 15/1484* (2013.01); *G01N 35/08* (2013.01); *B01L 2200/0652* (2013.01); *B01L 2200/0673* (2013.01); *B01L 2300/0627* (2013.01); *B01L 2300/0864* (2013.01); *B01L 2400/0487* (2013.01); *B01L 2400/0644* (2013.01); *G01N 2015/149* (2013.01); *G01N 2015/1481* (2013.01)

(56) References Cited

U.S. PATENT DOCUMENTS

| 2008/0053205 A1 | 3/2008 | Pollack et al. |
| 2016/0252446 A1 | 9/2016 | Smith et al. |

FOREIGN PATENT DOCUMENTS

| WO | 2008063227 A2 | 5/2008 | |
| WO | 2009011808 A1 | 1/2009 | |
| WO | WO-2009011808 A1 * | 1/2009 | ........... G01N 33/505 |
| WO | 20090050512 A2 | 4/2009 | |
| WO | 2010111231 A1 | 9/2010 | |
| WO | WO-2010111231 A1 * | 9/2010 | .......... B01F 13/0071 |
| WO | 2013018273 A1 | 2/2013 | |
| WO | 2015015199 A2 | 2/2015 | |

OTHER PUBLICATIONS

Wu, et al. Encapsulation of single cells on a microfluidic device integrating droplet generation with fluorescence-activated droplet sorting; Feb. 13, 2013; Biomed Microdevices (2013).

Medkova, et al, Analyzing Cancer at Single Cell Resolution with Droplet Technology; RainDance Technologies; http://raindancetech.com/rdt/wp-content/uploads/ May 2012.

Extended European Search Report; EP19156658.7; dated May 21, 2019; 8 Pages.

E. Brouzes, et al. "Droplet microfluidic technology for single-cell high-throughput screening," Proceedings of the National Academy of Sciences, vol. 106, No. 34, pp. 14195-14200; published Aug. 25, 2009.

European Extended Search Report for EPO Application No. 20206420.0-1101; dated Mar. 5, 2021; 9 pages.

\* cited by examiner

METHODS FOR PROCESSING DROPLETS CONTAINING BIOLOGICAL ENTITIES

FIELD OF THE INVENTION

This invention generally relates to systems and methods for providing a droplet containing one or more entities, in particular biological entities.

BACKGROUND TO THE INVENTION

In this specification we are concerned with emulsions, typically comprising microdroplets of water in oil, generally surfactant-stabilised. One or more biological entities such as one or more living cells or particles may be incorporated into each droplet and then experiments performed within the droplet, for example to perform a biological assay. Microdroplets can be generated and processed potentially at rates in excess of several thousand per second.

Typically the oil composition comprises a fluorous and/or mineral oil and, preferably, a surfactant, for example at around 0.5-5% vol/vol. Use of a fluorous oil is particularly advantageous when the microdroplets contain living entities because fluorous oil is good at transporting oxygen to the microdroplets. The surfactant may be either polymeric or small molecule; for example surfactants derived from block co-polymers of perfluoroethers such as Krytox™ or polyethylene glycol (PEG) may be used. The material or analyte within a microdroplet may comprise, for example, cells, DNA, protein, peptide, beads, particles, crystals, micelles, macromolecules, material for an enzymatic assay, organelles, an organism such as cell for example a mammalian cell, yeast cell, algal cell or bacterium, a virus, a prion and so forth. Typically a droplet has a diameter in the range 1-120 μm although droplets may be larger (or smaller), giving a volume which may be in the range nanolitres to femtolitres.

Integrated active elements on a microfluidic device can be used to control individual droplets—for example we have previously described in WO2009/050512, technology which enables the extraction on-chip of the contents of microdroplets by incorporating them into a continuous stream. Other general background prior art on microdroplets can be found in patents/applications in the name of RainDance Technologies Inc., for example WO2008/063227. Single cell or particle sorting is known from the prior art, for example US 2008/0053205; "Encapsulation of single cells on a microfluidic device integrating droplet generation with fluorescence-activated droplet sorting", Biomed Microdevices 2013, 15(3):553-60; "Analyzing Cancer at Single Cell Resolution with Droplet Technology", RainDance Technologies, URL: http://raindancetech.com/rdt/wp-content/uploads/2012/05/poster_analyzing_cancer_with_droplet_technology.pdf.

Whilst these techniques are useful, they can be extended. For example there is a class of difficult problems which involves diagnosing the biological behaviour in very rare biological entities or events, such as those associated with drug resistance. Another challenge is ensuring monoclonality: drug regulatory bodies often require that biopharmaceuticals and other chemical or biochemical entities are grown from a single, viable entity, or a specific combination of entities. This is because growing, for example, a cell population which stems from a single cell, or from a plurality of substantially identical, viable cells, ensures a high probability of monoclonality across the cell population. Yet another challenge involves selecting groups of cells for fermentation which have a high production yield.

There is a need for techniques which can be used to address these problems.

SUMMARY OF THE INVENTION

According to a first aspect of the present invention, there is therefore provided a method of providing a droplet containing one or more entities, the method comprising: providing a plurality of entities in a fluid; preparing a droplet from said fluid; determining whether said droplet contains one or more entities of said plurality of entities, or whether said droplet does not contain a said entity; sorting said droplet dependent on an outcome of said determination; and dispensing said sorted droplet into a reservoir, wherein said dispensing comprises, after said sorting: selecting a fluid flow path for fluid containing the sorted droplet; and ejecting the sorted droplet from the selected path.

The inventors have realised that the probability for obtaining a single entity, or a defined single combination of entities in a single droplet, for example a picodroplet (the volume of which is below approximately one thousand or a few thousand picolitres), may be increased using embodiments of this method. Each of the preparation, determination/sorting and dispensing steps of the method has a certain probability for obtaining one or more target entities in a single droplet. By combining these steps, the method allows for obtaining a single target entity or a single target combination of said entities in a single droplet with a probability of higher than 99.9%, in particular higher than 99.99%. For example this may be achieved with three stages of selection: encapsulation with Poisson statistics (as described later), sorting at a junction, and sorting/selection at the point of dispensing, each with, say, >90% selection. In a similar way, embodiments of the method facilitate extracting very rare target droplets from a large population.

We note that wherever references are made throughout the specification to a single (target) combination of entities, this may comprise a defined number of substantially identical entities (for example a defined number of a cell type), or a number of substantially identical entities within a defined range, or a combination of a defined number (specific or within a range) of a first entity (for example a defined number of a first cell type) and a defined number (specific or within a range) of a second or further entities (for example a defined number of a second or further cell type). Therefore, a target entity or entities in a droplet may be, for example: a defined number (greater than or equal to one) of entities of type A; a defined number (greater than or equal to one) of entities of type A and a defined number (greater than or equal to one) of entities of type B; a defined number (greater than or equal to one) of each of entities of three or more different types.

In a preferred embodiment the method further comprises identifying the sorted droplet for dispensing; extracting the sorted droplet from a first fluidic flow path of said fluid by transferring said sorted droplet from the first fluidic flow path into a second fluidic flow path; and ejecting the sorted droplet from the second fluidic flow path into the reservoir by applying pressure to the second fluidic flow path.

In one preferred embodiment of the method, the transferring comprises applying pressure to the sorted droplet for dispensing whilst in a portion of the first fluidic flow path and thereafter to transfer the sorted droplet from the first fluidic flow path into the second fluidic flow path and eject the sorted droplet. In embodiments the (water in oil) emulsion flows along the first fluidic flow path, through a shared region of flow path, and may then continue along the first flow path or be diverted into the second flow path by positive and/or negative (suction) pressure applied to the either flow path or to the shared flow path. Thus in embodiments the dispensing may employ a branched or T-junction channel arrangement with a shared region of flow, optionally but preferably in conjunction with a droplet selection/sorting mechanism for selecting a path.

This approach may, in embodiments, allow for a further sorting step of a droplet which was already sorted previously. A droplet may thereby be detected, and optionally its constituents analysed, prior to the second sorting step. The detection and/or analysis of the sorted droplet may thereby be performed at a shared flow path of the first fluidic flow path and a path at which pressure may be applied. Alternatively or additionally, the droplet may be detected and/or analysed prior to the shared flow path. In a preferred embodiment, the second fluidic flow path from which a droplet may be ejected may comprise first and second (or further) output channels. The pressure in the second output channel may be decreased (for example, by using a pump connected to the second output channel). A droplet may then be dispensed via the first output channel by applying pressure to the sorted droplet, as outlined above, whilst in the first fluidic flow path in response to a detection and/or analysis of the sorted droplet. This may ensure that the sorted droplet is not extracted into the second output channel using the pump. If a droplet is to be dispensed from the second output channel, e.g. if the droplet is not of interest, no pressure may be applied, such that the pump sucks the droplet into the second output channel. The analysis of a droplet to determine whether it is of interest may comprise an analysis as to a defined number of target entities in the droplet, and/or a property (e.g. fluorescence level, conductivity, and other physical or chemical properties) of the entity or entities in the droplet. An embodiment of such a channel network will be further described below.

In another preferred embodiment of the method, the dispensing comprises transferring the sorted droplet from the first fluidic flow path into the second fluidic flow path, then applying pressure to the second fluidic flow path to eject the droplet. This may be preferable as the flow of other droplets in the first fluidic flow path may not be disrupted due to the application of pressure in the second fluidic flow path only. Alternatively, however, dispensing of this type may employ a "decoupling unit" as described later to transfer move an unwanted droplet from the first fluidic flow path to a second, waste path when the droplet is unwanted, a droplet being dispensed from the first flow path by, for example, closing a valve in the first flow path and applying pressure to the emulsion to eject the droplet from a nozzle or the like at the end of the first flow path.

Embodiments of devices used to transfer a droplet from the first fluidic flow path to the second fluidic flow path will be further described below; for example a rotational unit, a translational unit or a decoupling unit as described later may be employed. Whether a droplet is to be transferred from the first fluidic flow path to the second fluidic flow path may be determined prior to the droplet entering the transfer unit, and/or while a droplet is in the transfer unit. The determination as to whether a droplet is to be transferred from the first to the second fluidic flow path may further be dependent on a defined number of target entities, and/or a property of the entity or entities in a droplet (e.g. fluorescence level, conductivity, and other physical or chemical properties).

In a preferred embodiment of the method, the extracting comprises extracting the sorted droplet only when the sorted droplet comprises a defined number of said entities, and/or when said sorted droplet comprises a said entity with a defined property. The defined number of entities may thereby be within a defined range. The defined property may be, for example, a physical property (e.g. a fluorescence level or other physical property) and/or a chemical property.

This may be preferable since the yield of droplets, which contain a target entity or entities, to be ejected into the reservoir, for example for further analysis and/or growth, may be increased. As outlined above, an entity being a target entity may thereby comprise the entity having a defined property, such as, but not limited to a physical property, and/or a chemical property, and/or the droplet containing a defined number of entities.

The number of entities in a droplet may, for example, be determined optically. The number of entities may alternatively or additional be determined by analysing a physical property (e.g. fluorescence level) and/or a chemical property of a droplet and/or entity (or entities), as the property may scale with the number of entities contained in a droplet. Physical and/or chemical properties may be determined using standard techniques.

Various methods and devices for preparing a droplet from a fluid may be used. Examples include, but are not limited to, T-junctions, Y-junctions, flow focusing devices, and others.

Whether a droplet contains one or more entities, in particular one or more target entities, or no entity, may be determined based on one or more of electrical, optical, thermal, acoustic, mechanical, temporal, spatial and other characteristics, for example other physical or chemical characteristics, of a droplet.

Techniques for sorting a droplet include, but are not limited to, magnetic field-based droplet sorting, dielectrophoresis, acoustic wave droplet sorting, and others.

The extracting and/or identification steps may allow for a further determination as to whether a single droplet contains one or more target entities, thereby increasing the probability for obtaining a single target entity or a single target combination of entities in a single droplet.

Embodiments of the method described herein are particularly suitable for increasing a monoclonality assurance of, for example, viable cells in a droplet, as will be further described below.

In a preferred embodiment of the method, wherein the ejecting comprises ejecting a said sorted droplet at a defined location in response to said determination and/or a property of a said entity. A sorted droplet may thereby be ejected, for example, into a well of a microtitre plate. The specific well of the microtitre plate into which a sorted droplet is to be dispensed is thereby chosen by the previously determined number of entities in a droplet (which may be a defined number of entities of one type or each of a plurality of types of entities), and/or by a property, for example a physical property (e.g. fluorescence level or other physical property) and/or chemical property of the entity or entities.

In preferred embodiments of the methods described herein a droplet has a volume of 50-1,000 picolitres, preferably 300-700 picolitres (fused droplets may be larger). Such volumes are preferable as they facilitate containing a single entity, or a small number of entities, of, for example a cell or biomolecule, while keeping consumable costs of fluids at a minimum, and in addition, smaller droplets facilitate faster processing. However larger droplets may be employed.

It may be preferable to grow and/or maintain, for example, microbiological cultures or cells. Therefore, in a preferred embodiment, the method further comprises incubating the droplet for growing and/or maintaining the one or more entities. As the probability for obtaining a single target entity or a single target combination of entities in a single droplet is, in embodiments, higher than 99.997%, the high monoclonality assurance allows for obtaining a large number of, for example viable cells when growing the one or more entities provided using embodiments of the method described herein.

The droplet may be provided to an incubator prior to the determination as to whether the droplet contains one or more entities (or no entity), and/or it may be provided to an incubator after the determination and sorting steps. Additionally or alternatively, the droplet may be incubated after the extraction step.

In a further preferred embodiment, the method further comprises performing a stability test on the one or more entities during the incubation. Performing a stability test on, for example one or more cells in a single droplet allows for sorting viable cells which have not degraded, altered production of a key analyte or biomolecule or died during the stability test. This allows for obtaining an even higher monoclonality assurance of, for example, viable cells or high producers or the key analyte or the like.

In a preferred embodiment of the method, the transferring of the sorted droplet from the first fluidic flow path into the second fluidic flow path comprises decoupling the sorted droplet from the first fluidic flow path in a decoupler, wherein the decoupler is configured to isolate a said sorted droplet from the first fluidic flow path and to guide a said isolated droplet to the second fluidic flow path.

In this way, a single droplet may be isolated from a fluid containing one or more droplets. The droplet may then be translated from one fluidic flow path to another, from where it may subsequently be dispensed, for example from a microfluidic chip on which the method is implemented. It may be particularly preferable to determine whether a droplet contains a viable single entity (or a specific combination or plurality of viable entities only), for example a viable single cell. This may allow for isolating from the fluidic merely droplets which contain viable single entities (or a specific combination or plurality of viable entities only). As a result, the monoclonality assurance for providing single droplets each containing a viable single entity (or a specific combination or plurality of viable entities only) may increase even further.

Ejecting the transferred droplet from, for example a microfluidic chip, may be particularly preferable as the one or more entities contained in the single droplet may be analysed further off-chip.

In a preferred embodiment of the method, the ejecting comprises heating a transport fluid (such as, but not limited to, oil) in which a said sorted droplet is transported. This allows for ejecting a droplet similar to the way in which a fluid is ejected from an ink-jet printer.

In a preferred embodiment, the method further comprises injecting a growth media fluid into the second fluidic flow path for ejecting the sorted droplet in the growth media fluid. This may be particularly preferable as, for example a population may be grown from the one or more entities contained in the single ejected droplet, and the ejected droplets may, for example, be ejected into a microtitre well in a growth media fluid for growing populations, for example cell populations or populations of biomolecules.

In a further preferred embodiment, the ejecting comprises ejecting the identified droplet via pressurised fluid ejection. This may be particularly preferable as droplets containing one or more entities, in particular one or more viable entities may be dispensed at a higher rate and/or in a controlled manner. It may, in this regard, be particularly important to isolate a droplet containing one or more viable entities from a first fluidic flow path of the fluid which carriers multiple droplets and to provide the droplet to a second flow path, as this allows for pressurised fluid ejection of a single droplet from the second flow path without affecting the flow of other droplets in the first fluidic flow path. A controlled ejection of, for example, one or more viable cells or biomolecules in a single droplet may thereby be achieved.

Methods and system described herein may be particularly suitable for cells and/or reagents, such as, but not limited to, biomolecules, since, as outlined above, the growth of for example cell populations may be required under statutory regulations to stem from a single, viable cell (or a number of only viable cells).

By providing methods and system described herein, consumable costs, in particular of fluids containing entities, and/or the time to deliver a lead drug may be reduced significantly.

In a preferred embodiment, the method further comprises: providing a second plurality of entities in a second fluid; preparing a second droplet from the second fluid; and fusing the first droplet prepared from the first fluid and the second droplet prepared from the second fluid to obtain a fused droplet; wherein said extracting comprises extracting the fused droplet by transferring the fused droplet from the first fluidic flow path into the second fluidic flow path. This may allow for obtaining a fused droplet which contains first and second cells, a cell and a reagent, and other combinations. Fusing the droplets may be performed using electrocoalescence, by electrically charging one or both of the first and second droplets, by passive or mechanical fusion, for example by providing flow channels with a shaped formation or other configuration to force droplets together, by employing chemically facilitated fusion, and/or using other techniques.

Fusing first and second droplets may therefore allow to, for example, investigate how a single cell (or a number of cells) reacts to a reagent. Furthermore, stability tests may be performed on a single cell (or a number of cells) being exposed to a reagent, or interactions between a single cell-pair (or combination of cells) may be analysed.

In order to fuse, for example a single cell (or cells) with a reagent, it may be preferable to first determine whether the first droplet contains a single entity (or number of entities) or not. Therefore, in a preferred embodiment, the determination and/or sorting are performed prior to the fusion of the droplets.

In a further preferred embodiment, the method further comprises: determining whether the second droplet contains one or more entities of the second plurality of entities, or whether the second droplet does not contain a said entity of the second plurality of entities; and sorting the second droplet dependent on an outcome of the determination. This allows to, for example, ensure that the first droplet is fused with a second droplet only if the second droplet contains one or more target entities. Preferably, the fusing is performed only for a said first droplet and a said second droplet which have been determined to contain one or more target entities of the first and second pluralities of entities, respectively.

Embodiments of the method therefore allow, for example, for analysing a single pair of cells, or a single pair of a cell and a reagent, such as a biomolecule, or a single target combination of one or more cells with one or more reagents, which are contained in a single droplet.

Therefore, in a preferred embodiment of the method, the fused droplet contains a single pair of two cells, or a single pair of a cell and a reagent, or a single combination of one or more cells, or a single combination of one or more cells with one or more reagents, in particular wherein the reagent is a biomolecule. It will be appreciated that other combinations of a single pair of two entities contained in a single droplet may be analysed and/or further processed using embodiments of the method described herein.

The skilled person will appreciate that methods may also be used for combining multiple entities/reagents.

In a further preferred embodiment of the method, the sorting comprises detecting a said droplet at a plurality of locations of said fluid flow path at different points in time to determine a velocity of a said droplet in said fluid flow path for timing said sorting. Embodiments of the method allow for improved control of sorting the droplet(s) as a certain location of the droplet(s) in the fluidic flow path can be determined and/or predicted. Thus, for example, a pair of sensors, such as light gate sensors, may be used to estimate the speed of travel of a droplet. The position of the droplet at a future time may then be predicted. This may be used, for example, to check that a droplet is present in or has been directed/sorted into a correct channel, by checking that a droplet is present at the expected time and place.

In a related aspect of the invention, there is provided a method of preparing a droplet containing a single pair of two biological entities, the method comprising: providing a first plurality of biological entities in a first fluid and providing a second plurality of biological entities in a second fluid; preparing a first droplet from the first fluid and preparing a second droplet from the second fluid; determining whether the first droplet contains a single entity of the first plurality of biological entities and whether the second droplet contains a single entity of the second plurality of biological entities; and fusing the first droplet and the second droplet which have been determined to contain a said single entity, respectively. The probability for obtaining a single pair of two entities in a single droplet may therefore be increased, as the determination step, in this example, for both of first and second droplets, respectively, is performed prior to fusing the droplets.

Preferred embodiments of the above-described first aspect of the invention equally apply here. Therefore, for example, the fused droplet may then be extracted from a first fluidic flow path of the fluid by transferring the sorted droplet from the first fluidic flow path into a second fluidic flow path. Preferably, the first and second droplets may each go through all the steps of the above-described first aspect of the invention, and preferred embodiments thereof. The probability for obtaining a fused droplet which contains a single pair of entities from the first plurality of biological entities and the second plurality of biological entities, respectively, may thereby be significantly increased.

Fusing the droplets may be performed by electrocoalescence, by electrically charging one or both of the first and second droplets for fusing the droplets by electrostatic attraction, by passive or mechanical fusion, by chemically facilitated fusion, or by other techniques.

In a related aspect of the invention, there is provided a method of metabolising and/or analysing a biological entity contained in a droplet, wherein the biological entity comprises a single cell, or a single pair of two cells, or a single pair of a cell and a reagent, the method comprising providing the biological entity contained in the droplet using the method of any one of the aspects and embodiments described above.

The metabolising (growing) may comprise increasing an entity in number, for example in the case of bacteria, or may comprise allowing an entity such as a mammalian cell to metabolise, for example to produce a product.

Since embodiments of the method described herein result in a very high monoclonality assurance, they are particularly suitable for growing, for example, a single cell (or biomolecule, or another entity) contained in a single droplet, because cells in a cell population grown from a single cell have a very high probability of all being substantially identical to each other. Similarly, analysing a single cell in a single droplet allows for ensuring that any measurements are performed on the cell of interest. This may not be guaranteed for a large number of cells contained in a single droplet since, for example, mutations may result in a statistical distribution of cells (or other entities) which may not all be substantially identical.

In a further aspect of the invention, there is provided a microfluidic system for providing a droplet containing one or more entities, the system comprising: a droplet formation device for preparing a droplet from a fluid which contains a plurality of entities; an analyser for determining whether a said droplet contains one or more entities of the plurality of entities; a droplet sorting device for sorting a said droplet dependent on an outcome of the determination; and a decoupler for decoupling a said sorted droplet from a fluidic flow path of the fluid in the microfluidic system.

In preferred embodiments, the microfluidic system further comprises a further analyser configured to identify a said decoupled droplet (or a said sorted droplet which has been transferred from a first fluidic flow path into a second fluidic flow path via, for example, the decoupler), and a droplet dispensing unit which is configured to eject the identified droplet into, for example, a reservoir (e.g. a microtitre plate).

Preferably, the analyser(s) is (are) configured to determine whether a droplet contains a single target entity of a plurality of entities and/or whether the droplet contains a single target combination of entities of a plurality of entities.

Embodiments of the microfluidic system therefore allow for obtaining a single entity, for example a single cell or a single pair of biological entities, in a single droplet, or a single target combination of entities. Each of the droplet formation device, the analyser and droplet sorting device, and the decoupler allow for obtaining one or more target entities in a single droplet with a certain probability. The combined probability for obtaining a single entity or a single combination of entities in a single droplet using embodiments of the microfluidic system may be higher than 99.9%, in particular higher than 99.99%. The decoupler may thereby comprise an analyser for a further determination as to whether a single droplet contains a single entity.

In a preferred embodiment of the microfluidic system, the decoupler comprises an isolation unit for isolating a said sorted droplet from the fluidic flow path and a guide for guiding a said isolated droplet into a second fluidic flow path of the microfluidic system. This may be particularly preferable since a single entity (or a single combination of entities) contained in a single droplet may then be isolated and dispensed and/or analysed separately from other droplets or fluid.

In a further preferred embodiment of the microfluidic system, the guide comprises a rotating unit, wherein the rotating unit comprises a droplet storage unit for storing a said isolated droplet, and wherein the rotating unit is configured to be rotated to transport a said isolated droplet stored in the droplet storage unit into the second fluidic flow path.

Once a droplet containing an entity (or a plurality of entities) of interest has been detected, the droplet may be placed in the droplet storage unit, and the rotating unit may be rotated to then provide the droplet to the second fluidic flow path. In some embodiments, the rotating unit completes the first and second fluidic flow paths.

In some other embodiments a branched flow channel may be used for a similar purpose, more particularly for selecting/dispensing droplet.

In some embodiments, the droplet storage unit may be a channel which completes the first and second fluidic flow paths, respectively.

In a further preferred embodiment of the microfluidic system, the guide comprises a translational unit, wherein the translational unit comprises a droplet storage unit for storing a said isolated droplet, and wherein the translational unit is configured to be moved in a translational direction to transport a said isolated droplet stored in the droplet storage unit into the second fluidic flow path.

Similarly to the rotating unit, once a droplet containing an entity (or plurality of entities) of interest has been detected, the droplet may be placed in the droplet storage unit of the translational unit, and the translational unit may be moved to then provide the droplet to the second fluidic flow path. In some embodiments, the translational unit completes the first and second fluidic flow paths.

In some embodiments, the droplet storage unit may be a channel which completes the first and second fluidic flow paths, respectively.

In a preferred embodiment, the guide may be configured such that it combines an input channel with two or more output channels. A channel of the guide may thereby be moved in a swinging-like motion, allowing connecting of an input fluidic flow path with a plurality of output fluidic flow paths.

In a preferred embodiment, the microfluidic system further comprises an incubator for incubating the droplet for growing and/or maintaining the one or more entities. As outlined above, as the probability for obtaining a single target entity or a single target combination of entities (which may be a plurality of substantially identical entities) in a single droplet is, in embodiments, higher than 99.99%, the high monoclonality assurance allows for obtaining a large number of, for example viable entities (e.g. cells, biomolecules or other entities) when growing the one or more entities using embodiments of the microfluidic system described herein.

The incubator may be placed in front of the analyser in a fluidic flow path direction, and/or it may be placed behind the analyser and droplet sorting device in a fluidic flow path direction. Additionally or alternatively, the incubator may be placed behind the decoupler in a fluidic flow path direction in the microfluidic system.

In a preferred embodiment of the microfluidic system, the incubator comprises a stability test unit for performing a stability test on the one or more entities during the incubation. Performing a stability test on one or more entities, for example a cell (or cells), in a single droplet allows for sorting viable entities which have not degraded, changed production of a key analyte or biomolecule or died during the stability test. This allows for obtaining an even higher monoclonality assurance of viable entities, such as, but not limited to viable cells, biomolecules and other entities and/or cells that produce high levels of the key analyte or the like.

In a preferred embodiment, the microfluidic system further comprises a dispensing unit for dispensing the decoupled droplet. The decoupled droplet may thereby be dispensed into, for example, individual wells of a microtitre plate where the one or more entities contained in the single droplet (or multiple droplets) may be stored and afterwards retrieved for further processing or analysis, or for subsequent use, for example in fermenting or the like.

In a further preferred embodiment of the microfluidic system, the dispensing unit comprises a reservoir for storing a growth media fluid, and wherein the dispensing unit is configured to dispense a said decoupled droplet in the growth media fluid. This may be particularly preferable, as the dispensing step and the step of placing the single droplet containing the one or more entities in a growth media fluid may be combined in a single step. A droplet may be prepared from the growth media fluid which contains the entity or entities-containing droplet, which may then be dispensed into, for example individual wells of a microtitre plate.

In a preferred embodiment of the microfluidic system, the dispensing unit comprises an increased (or decreased) pressure unit for dispensing the droplet via pressurised fluid ejection. The change in pressure may be produced by many techniques including, but not limited to: piezoelectric, thermal, and pressurised gas methods. Ejecting a droplet via pressurised fluid ejection may be particularly preferable, since the time to dispense a droplet from the microfluidic system may be significantly shortened, and/or the ejection via different outputs may be controlled, as will be further described below. By isolating or decoupling a droplet of interest which is to be dispensed from the microfluidic system from the first fluidic flow path, merely the droplet to be dispensed is exposed to the high pressure unit. It may be preferable to only expose a decoupled droplet to the high pressure unit, as a droplet analysis and sorting in the analyser and the droplet sorting device may be difficult to achieve for droplets being exposed to a high pressure unit.

In a preferred embodiment of the microfluidic system, the droplet formation device comprises a plurality of droplet formation devices, and wherein the microfluidic system further comprises a droplet fusion device for fusing a plurality of droplets prepared using the plurality of droplet formation devices. Embodiments of the microfluidic system therefore allow for preparing assays of, for example, a single pair of cells, or a single pair of a cell and a reagent, or a single combination of specific entities contained in a single, fused droplet.

The droplet fusion device may be placed in front of the analyser and droplet sorting device in a fluidic flow path direction in the microfluidic system. Preferably, the droplet fusion device may be placed behind the analyser and droplet sorting device in a fluidic flow path direction, as this allows for fusing only droplets which have been determined to contain one or more target entities of a first and second plurality of entities, respectively.

The droplet fusion device may alternatively be placed behind the decoupler. An advantage of doing so is that the probability of two droplets each containing one or more entities of interest may be comparatively high prior to fusing those droplets.

The droplet fusing device may comprise an electric field generator for generating an electric field for fusing the droplets by electro-coalescence. Alternatively or additionally, the droplet fusion device may comprise one or more charging devices for electrically charging droplets. Fusion of droplets is thereby promoted via electrostatic attraction of droplets. Droplet fusion may alternatively or additionally be achieved by providing a droplet fusion device which comprises channel geometries which allow for passive droplet fusion, for example via channel constructions at which a droplet may impact onto another droplet to thereby fuse with the other droplet.

In a preferred embodiment of the microfluidic system, the analyser comprises one or more of a fluorescence detector, a scattered light detector, an acoustic wave generating and detecting unit, and a magnetic-activated cell sorting device. The content of a droplet may be determined via one or more of these devices, and the droplet may be sorted in the droplet sorting device according to the determination. It will be understood that one or more particular methods or devices for analysing the content of a droplet may be preferred over other methods or devices depending on the target content which is to be detected in a droplet.

In a further preferred embodiment of the microfluidic system, the analyser and/or droplet sorting device comprises a plurality of sensors for detecting a said droplet at different locations of said microfluidic system (at different points in time) to determine a velocity of said droplet in said microfluidic system, and wherein said droplet sorting device is configured to sort said droplet dependent on an outcome of said velocity determination. This allows for an improved sorting of the droplet(s) as the location of the droplet(s) in the fluidic flow path of the microfluidic system can be determined and/or predicted.

In a further aspect of the invention, there is provided a droplet sorting or dispensing device comprising a substrate bearing: a set of one or more microfluidic input channels; a set of microfluidic output channels; a moveable sorting element between the input channels and the output channels, wherein the sorting element comprises a set of microfluidic channels to connect the input channels to the output channels, and wherein the sorting element is moveable between a first position in which at least a first said input channel is connected to allow fluid flow from the first input channel to a first said output channel and a second position in which a length of fluid in a said channel and bearing one or more droplets is moved such that the length of fluid flows into a second said output channel.

Embodiments of the droplet sorting/dispensing device therefore allow for extracting a droplet from a first fluidic flow path by transferring the droplet from the first fluidic flow path into a second fluidic flow path. Hence, the droplet sorting device may be used to connect and/or complete microfluidic channels of a microfluidic device. As outlined above, this may be particularly preferable as a droplet may be decoupled from the first fluidic flow path of the microfluidic system, and dispensed from the system by, for example, pressurised fluid ejection from the second fluidic flow path.

In a preferred embodiment of the droplet sorting/dispensing device, the sorting element is rotatable between first and second positions to swop lengths of fluid from first and second input channels so that they flow either to respective first and second output channels or are swopped to flow to respective second and first output channels. A prior determination as to the constituents of a droplet may therefore allow for sorting droplets by extracting a droplet of interest (or alternatively a droplet which is not of interest) from a first fluidic flow path and provide it to a second fluidic flow path based on the determination.

Embodiments of the droplet sorting/dispensing device therefore allow for extraction of a droplet from a fluidic flow path without disrupting the fluidic flow path within a microfluidic system.

In a related aspect of the invention, there is provided a method of sorting or dispensing droplets, the method comprising: providing first and second microfluidic flows, at least one of said flows containing droplets; and rotating a turntable comprising portions of said flows to selectively direct droplets to one of first and second output microfluidic flows. Embodiments of the method therefore allow for sorting droplets, for example based on a prior determination as to the properties of the droplets and/or their contents.

In a related aspect of the invention, there is provided a device for sorting or dispensing droplets in microfluidic flows, the device comprising: first and second input microfluidic flows, at least one of the flows containing droplets; first and second output microfluidic flows; and a rotating turntable comprising portions of flows between the input and the output flows; and a controller to control rotation of the turntable to selectively direct the droplets to the first and second output microfluidic flows.

Once a droplet enters from, for example, the first input microfluidic flow into one of the portions of flows of the rotating turntable, the turntable may be turned such that the droplet may exit at the second output microfluidic flow. If, based on a previous analysis of a droplet and/or its content(s), it is desired to maintain the droplet in a channel, the turntable is not turned so that the droplet flows, for example, from the first input microfluidic flow via a portion of flow of the rotating turntable to the first output microfluidic flow.

In a related aspect of the invention, there is provided a cell, biomolecule and entity sorting or dispensing device for transferring a picodroplet from a first fluidic flow path to a second fluidic flow path, the sorting device comprising: a decoupler for decoupling a said picodroplet from a said first fluidic flow path; and a guide for guiding a said decoupled picodroplet to a said second fluidic flow path, wherein the guide comprises: a rotating unit configured to be rotated for transporting a said decoupled picodroplet to a said second fluidic flow path; and/or a translational unit configured to be moved in a translational direction for transporting a said decoupled picodroplet to a said second fluidic flow path. As to whether a droplet is to be decoupled and guided from the first fluidic flow path to the second fluidic flow path may have been determined prior to the droplet entering the sorting device. Alternatively or additionally, this determination may be made when a droplet is inside the sorting device.

In a preferred embodiment, the cell, biomolecule and entity sorting device further comprises an x-y moving platform comprising one or more microtitre plates, and/or one or more glass slides, and/or one or more arrays or other formats onto which one or more of the picodroplets are dispensable at one or more addressable locations. The droplets may therefore be dispensed into the one or more individual wells of microtitre plates, and/or one or more glass slides, and/or one or more arrays or other formats according to a predefined pattern, and the droplets and its contents may then be analysed and/or processed further, for example to grow populations.

Embodiments of the droplet sorting/dispensing device, and/or embodiments of the cell, biomolecule and entity sorting/dispensing device described herein may be incorporated into a droplet dispenser, in particular a picodroplet dispenser. Such a droplet dispenser is configured to selectively dispense a selected (sorted) droplet from a microfluidic channel into a reservoir.

Furthermore, embodiments of the droplet sorting/dispensing device, and/or embodiments of the cell, biomolecule and entity sorting/dispensing device, and/or embodiments of the picodroplet dispenser described herein may be implemented into a microfluidic device.

Cartridges

In a further aspect the invention provides a microfluidic cartridge for automated sorting and dispensing of sorted microfluidic droplets, the cartridge comprising: a sorting input channel coupled to a sorting region, said sorting region comprising two or more sorting output channels coupled to said input channel and a droplet director to selectively direct a droplet from said sorting input channel to a selected one of said sorting output channels; and a droplet dispenser coupled to one of said sorting output channels to dispense selected said droplets from said cartridge for collection in a reservoir, wherein said droplet dispenser comprises a droplet ejection mechanism to eject droplets from an emulsion flow into a dispenser output channel for collection in said reservoir.

Embodiments of such a cartridge provide a disposable/consumable device which can be used to address a number of important problems, such as identifying and collecting a target which may only be present in one in $10^6$ or $10^9$ droplets, for example a drug-resistant bacterium. In broad terms this may be done by identifying a signal from the droplets of interest and then collecting these droplets for further analysis, in principle in a common reservoir but in some preferred embodiments in separate, identifiable reservoirs. This latter approach allows cells or other entities with individually identified properties to be retrieved from, say, a multi-well plate for subsequent analysis or use—effectively individual wells of such a multi-well reservoir may be used to collect individual entities with selected properties.

In a complementary manner, rather than being used directly for an assay embodiments of the cartridge may be used in a 'stability test mode' to identify changed (for example, negative) responses in a population of droplets (for example cells) which are notionally all identical. As an example, in this mode of operation the cartridge can be used, for example, to identify individual instances where production of a substance by a cell has been switched off, say to troubleshoot falling yields in a fermentation batch.

In preferred embodiments the cartridge includes an incubation region or chamber where droplets can be held, preferably at a controlled temperature to allow incubation of the contents of the droplet prior to controlled release. In embodiments this region is configured to hold the droplets at a greater density than when dispersed within the emulsion; this may be achieved by holding the droplets (which typically 'float') in an upper portion of the chamber and providing a valve or similar at the top of the chamber for controlled release of the droplets—in use the cartridge is orientated with the top of the incubation chamber upwards. Excess carrier fluid (oil) may be released to waste. Preferably, but not essentially, the incubation region is upstream of the sorting region.

As the skilled person will appreciate the emulsion (which may be a double emulsion) is generally a water-in-oil emulsion. The cartridge is preferably configured to interface with a microdroplet processing system—that is in embodiments the cartridge can be attached into and released from the microdroplet processing system, which provides sensing and control functions. In embodiments the microdroplet processing system provides temperature control for the incubation chamber and droplet property sensing for droplet sorting, and may also provide relative motion between the dispenser output channel and reservoir wells to collect the droplets.

In a typical embodiment the cartridge generally has the form of a flat plate bearing microfluidic channels, one or more holding regions, valves and the like. It is preferably substantially optically transparent, and may be fabricated from a range of plastic materials, for example polydimethylsiloxane (PDMS) or cyclic olefin polymer or copolymer (COP or COC). The cartridge may then be mounted vertically or at a suitable angle in the system/instrument with the dispenser output channel directed downwards towards a multi-well or microtitre plate. The instrument may then move the cartridge and/or plate to direct the output channel into a selected well.

In preferred embodiments the cartridge is provided with a plurality of fluidic connections, which may be made automatically when the cartridge is inserted into the instrument. Generation of the emulsion may be performed on-cartridge or off-cartridge. For example, in embodiments the cartridge may be provided with reservoirs along one edge (so that these are in the correct orientation when the cartridge is vertical), to hold oil and aqueous medium (such as water and growth medium) for droplet-on-chip droplet generation.

Embodiments of the microfluidic cartridge are, are previously described, directed towards identifying a very few, extremely rare droplets containing a biological entity of interest from a very large population. The droplet sorter may operate one or two orders of magnitude faster than the droplet dispenser—for example the dispenser may operate at 1-10 Hz whereas the sorter may operate at 100-1,000 Hz. Nonetheless, because of the statistics of the target entities, the dispenser may not operate continuously. Thus, in some preferred implementations of the cartridge one or more emulsion flow buffer regions are provided between the sorting region and the dispensing region of the cartridge, to control an emulsion flow rate to the droplet dispenser. In embodiments such a buffer region may comprise a chamber, somewhat akin to the incubation region previously described, where droplets can accumulate whilst excess oil is siphoned off or released to waste. For example droplets may be allowed to float to the top of the chamber from where they can be released in a controlled manner by a valve or the like. Where a buffer region is included, in embodiments this may comprise a length of microfluidic channel, for example in a serpentine configuration, arranged so that an order of the droplets is maintained. In this way the identity of a droplet having a droplet characteristic measured upstream of the buffer may be maintained since the order or sequence of droplets is maintained. In other arrangements, however, a widened channel or chamber may be employed, which has the advantage of facilitating the provision of a larger capacity. In this case the characteristics of droplets may be measured after their exit (in sequence) from the buffer region. In both cases, preferred embodiments link one or more characteristics of a droplet to an identifiable property of a droplet, typically its position, so that when the droplets are dispensed into wells/reservoirs the properties of the droplet(s) within a well/reservoir are known.

Thus in preferred embodiments of these and the other methods/apparatus described herein, the contents of a dispensed droplet in an identified well/reservoir are known and stored for later use. In this way droplet contents (for example a cell, protein, antibody, reagent or analyte) with a desired/target property can be retrieved after droplet dispensing by retrieving the contents of a well/reservoir known (recorded) to have contents with the desired/target properties.

In some preferred embodiments the output channel of the dispenser includes a mechanism to promote liberation of a droplet, or the contents of a droplet, from the emulsion. As previously mentioned, the contents of a droplet typically comprise water and a biological entity, such as a cell, often in a growth medium. The purpose of the cartridge is to extract those (rare) biological entities which have a particular property or characteristic, and this is done by collecting target droplets in one or more reservoirs, which may already contain, say, 20-50 µl of water/growth medium in the well of a microtitre plate. By comparison an ejected slug of emulsion may have a volume of 50-300 nl (depending in part upon the channel width) whilst a droplet may have a volume of order 50 pl or larger. In practice it has been found that when a slug of emulsion is ejected from the dispenser output channel the water from a droplet, and its contents, may end up floating on the surface of the oil (depending in part upon the oil density and upon whether or not it is fluorinated). Embodiments of the droplet ejection mechanism therefore preferably comprise a system to extract the droplet from the emulsion and/or to break up a droplet. This may be achieved mechanically by shaping, for example narrowing, a nozzle of the dispenser output channel and/or by providing a mesh across the output channel; and/or this may be achieved electrically, for example by providing a pair of electrodes adjacent the exit of the dispenser output channel across which a voltage can be applied to generate an electric field to disrupt the emulsion/droplet; and/or a chemical mechanism may be employed, for example by adding a stream of de-emulsification agent such as perfluorooctanol into the dispenser output channel.

In some preferred embodiments, the microfluidic cartridge further comprises a plurality of sensors for detecting a said droplet at different locations of said microfluidic cartridge (at different points in time) to determine a velocity of said droplet in said microfluidic cartridge, and wherein said droplet director is configured to direct a said droplet dependent on an outcome of said velocity determination. This may be particularly advantageous as the location of the droplet(s) in the cartridge may be determined and/or predicated to further improve control over sorting the droplet(s) in the sorting region.

In some preferred embodiments the droplet ejection mechanism comprises a mechanism to increase a pressure in the emulsion flow to direct droplets into the dispenser output channel. In some embodiments this may be achieved by arranging the dispenser output so that it has a main channel and a side channel (in a form of T-junction, as described later) and then applying a pressure pulse to drive a droplet into the side channel (dispenser output channel) for output. In one embodiment such an arrangement may comprise a pair of valves, such as pinch valves, along the length of an emulsion flow with the side channel (dispenser output channel). In this way the valves can be closed to isolate the flow and then pressure applied to the isolated slug of emulsion, to drive the emulsion containing the droplet into the dispenser output channel. In another approach a slug of emulsion may be transferred from a first channel/flow to a second, where a pressure pulse may be applied to eject the slug and its associated droplet. The skilled person will recognise that other configurations are possible. A suitable pressure pulse may be provided mechanically, for example using a piezoelectric transducer. Alternatively a pressure pulse may be generated electrically, for example by means of an electrical heating element and bubble expansion (in a similar manner to an ink-jet printer). In some preferred embodiments an increased pressure pulse is applied to eject a slug of emulsion with its droplet, but the skilled person will appreciate that in principle the arrangements we describe later may be adapted so that instead a pulse of reduced pressure is used to eject droplets from an emulsion flow into the dispenser output channel.

In some preferred implementations it is convenient to physically separate the droplet ejection mechanism from the system used to sense/detect the presence of a droplet for ejection. In embodiments this is achieved by using the instrument housing the cartridge (microdroplet processing system) to sense one or both of the position and the speed of a droplet selected by the sorting system for ejection. The sensing may be performed upstream of the droplet ejection mechanism so that the position of the droplet can be predicted when the droplet reaches the ejection mechanism. In principle droplet speed need not be measured if the rate of flow of emulsion can be controlled sufficiently accurately, but in practice measuring the speed is advantageous. It is further advantageous to control the channel size tolerance, to reduce variations in channel size and hence droplet speed variations. Imaging the droplets in a separate location to the droplet ejection mechanism in this manner makes the cartridge/instrument simpler and more effective.

As previously mentioned, in some preferred embodiments droplets are dispensed into individual wells of a microtitre plate or the like, comprising a plurality of separate wells. The instrument (microdroplet processing system) may then comprise a control system to selectively direct a dispensed droplet to a reservoir. In embodiments either the cartridge or the multi-well plate is mounted on an X-Y moveable stage so that the cartridge and plate may be moved relative to one another to direct the dispenser output channel to a selected reservoir. As previously mentioned, a well may hold one or more droplets, depending upon the application/assay/mode of operation of the instrument.

In some preferred implementations, when one or more properties of a droplet are interrogated by the instrument for sorting corresponding data is stored for a selected, target droplet with desired properties. This data is then associated with information identifying a particular well or reservoir into which the droplet is dispensed. In this way a droplet with particular properties can afterwards be retrieved from its reservoir for later analysis and/or a multi-well reservoir can be used to extract a set of droplets with a particular property or range of properties. Although the sorting may be based on, say, comparison of a measured value with a threshold value it is possible for the selected droplets to have a range of values of a parameter, which may in turn correlate with some other property measuring activity of the biological entity within the droplet. It is therefore useful to be able to link a measure of one or more parameters with a droplet in a particular well of the reservoir. Examples of properties which may be sensed by the instrument include (but are not limited to): an optical property such as one or more of a degree of fluorescence, a degree of scatter, a degree of luminescence, a degree of absorbance; electrical or magnetic properties such as an electrical conductance; and or one more derived or inferred properties, such as whether a cell is living or dead (which may be inferred from an optical measurement). The skilled person will recognise that although it is convenient in embodiments to sense one or more properties of an individual droplet when sorting the droplets, in principle the sensed data stored in association with reservoir identification data may additionally or alternatively be sensed after sorting, by a separate arraignment of sensors. In both cases embodiments of the combined cartridge and instrument facilitate tracking of individual dispensed droplets for later analysis or use.

As previously described, uses to which embodiments of the cartridge may be put include a direct droplet assay and a biological entity stability/viability assay. In some applications an assurance of monoclonality is important—that is, it can be desirable for individual reservoirs/wells which contain a biological entity such as a cell to contain just a single such entity. This is important, for example, where an antibody is being generated from a cell line—it can be important for regulatory purposes to be able to substantially guarantee that an antibody has been derived from a single clone of cells if, say, the antibody is being used to create a drug. For these applications the incubation chamber is generally not needed, and thus a cartridge version without such a chamber may be employed. Alternatively, a more generic cartridge may be provided in which the incubation chamber may be bypassed or, in another version, droplets may be passed through the incubation chamber as previously described but without incubation.

One way in which embodiments of the microfluidic cartridge may be used for monoclonality assurance is to use the droplet sorter to select droplets containing just a single cell, sending empty droplets and droplets with two or more cells to waste. The number of cells in a droplet may be determined optically, for example by detecting optical absorbance, scattered light, fluorescent light, or (in some preferred embodiments) by visualising and counting individual cells within a droplet. Such an approach is facilitated by generating droplets with a strong statistical bias towards creating empty droplets. Typically a droplet generation system employs flow focusing and generates droplets containing a number of biological entities which obeys Poisson statistics. Monoclonality assurance is facilitated by operating such a system so that less than half the droplets contain a biological entity, preferably less than 30%, 20% or 10%—for example the system may be operated so that only around 5% of the droplets contain a single entity/cell.

These techniques together can provide substantial assurance of monoclonality—that is that there is no more than a single cell per well/reservoir. However, in embodiments still further assurance is desirable, and this can be provided by adding a second sorting stage following the first stage—even though, in theory, the first stage should permit only droplets containing a single biological entity/cell to enter the selected output channel. In embodiments this second sorting stage may effectively be combined with the droplet dispenser—that is the dispenser may, in embodiments, be configured to itself select droplets with a defined number (or numeric range) of biological entities per droplet. Thus the droplet ejection mechanism may be selective, dependent upon confirmation that that a droplet contains only a single biological entity or, more generally, a defined number or numeric range of biological entities. Conveniently, detection of the number/number range of entities per droplet may be made by the sensor(s) employed to sense the speed/position of a selected droplet, as previously described. In this way an extremely high degree of monoclonality assurance can be provided.

Although we have described the particular application of monoclonality assurance, the above described techniques may be adapted to target a defined number of biological entities per droplet rather than particularly a single entity per droplet. For example when manipulating droplets containing bacteria rather than, say, mammalian cells, a numeric range is more appropriate; this may define a few tens of organisms per droplet, for example 25-35 entities per droplet.

In a still further application of the technology a microfluidic cartridge of the general type described above may provide a 'fusion assay' or functional assay mode of operation.

To provide this mode of operation the microfluidic cartridge is provided with a droplet fusion region having at least two input channels and at least one output channel to provide an input to the sorting region (the incubation region, where present, may be either before or after the sorting region). As the skilled person will be aware, there are many techniques for fusing microdroplets, including physical fusion techniques and techniques employing an electric or other field to cause droplet fusion (some examples are described in our earlier filing, WO2009/050512 (hereby incorporated by reference). In broad terms the droplet fusion region is used to combine biological entities upstream of the sorting region so that a fused droplet may be selected based on a potentially rare interaction between the combined entities. As previously described the two (or more) emulsions comprising the droplets to be fused may be generated on or off the cartridge. In some preferred embodiments such a system can be used to identify very rare cases when one biological entity is resistant to another, potentially down to a probability of one in one million or one in one billion. Thus, examples may comprise a T-cell resistant to infection by HIV or a bacterium resistant to a phagocyte; the skilled person will readily be able to appreciate that embodiments of the system may be used to identify other similar situations. Again as the skilled person will be aware cell sorting may be based upon any of a variety of physical properties, typically optical properties; in one approach a determination is made of whether an entity within a droplet is alive or dead.

Although we have described a sorting region with two output channels, in principle three or more output channels may be provided, for example to sort a mixed population of entities into groups or categories (sorting into multiple channels may be achieved, for example, by selectively directing droplets using pairs of electrodes to apply an electric field). For example in a population of cells intended for fermentation the population may be sorted into groups of high, medium and low productivity and it may be, for example, that the cells with medium productivity are more desirable than those with high productivity because they are subsequently more robust in a large scale fermentation system. Thus, it will be appreciated that in such an arrangement any one or more of the output channels may be employed for collecting the contents of selected droplets for further processing/analysis.

In embodiments of the cartridge in use broadly speaking a sample, and oil are loaded into separate sterile reservoirs on one edge of the cartridge (the cartridge is mounted vertically or at a suitable angle) and an emulsion is generated. The emulsion is pumped to the incubation chamber where the droplets float upwards and the excess oil runs to waste. The incubation chamber is then heated, for example to 37° C. for some period of minutes to hours, and then cooled, for example to around 8° C., to limit metabolism. The droplet population is then moved (pumped) to the sorting region where target droplets are selected and moved from there to a holding region, again removing excess oil (syphoning off or allowing the excess to run to waste) droplets are then released one by one from the holding region (additional oil is added to facilitate this process) and moved to the dispensing region where the droplet ejection mechanism ejects selected droplets into a common or individual reservoirs for the droplets.

We have described cartridges which may have a number of droplet processing regions, in particular for droplet generation, droplet incubation, droplet sorting, droplet holding ("buffering"), and droplet dispensing. In embodiments the cartridge is provided in a modular form, having a base or substrate to which separate modules to perform some or all of these functions may be attached as desired. This may be facilitated by having a standard interface or set of interfaces between modules of such an arrangement.

In a related aspect of the invention, there is provided a microfluidic system for providing one or more target entities in a droplet, the microfluidic system comprising: a first detector for detecting one or both of: whether a said droplet contains a said target entity or target entities; and a property of a said target entity or target entities; the microfluidic system further comprising: a sorting device for sorting a said droplet dependent on an outcome of said detection; and a droplet dispensing unit for dispensing a said sorted droplet at one or more target locations, wherein said microfluidic system is configured to correlate a said target location with a said property of a said target entity or target entities detected in said first detector.

The droplets may thereby be dispensed into individual wells of a microtitre plate, or onto another medium. Since a droplet may be dispensed based on the detection in the first detector, a droplet at a specific target location (which may, for example, be a well of a microtitre plate) may be correlated to the properties of a droplet as a whole and/or its constituents (if any). These properties may be, but are not limited to one or more of a level of fluorescence, a level of scatter luminescence, an absorbance level, a conductivity level, and other chemical and/or physical properties. Thus, for example, embodiments of the methods/systems we describe, according to both this and other aspects of the invention, can be used to determine which droplet/reservoir (for example which well of a multi-well plate) has which properties. This may be used later to identify, and more particularly be able to provide a sample, of a cell or biological entity responding in a particular way to whatever assay or test is being performed by the microfluidic system (because a target entity/droplet with identified properties is held within an identified well, and because, in embodiments, a record of log is kept of which droplet/cell/entity is dispensed into which reservoir/well).

Alternatively, the sorted and analysed droplets may be dispensed into a single reservoir.

It may be preferable to perform one or more further analysis of a droplet and/or its constituents before a decision may be made as to which target location a droplet may be dispensed into.

Therefore, in a preferred embodiment, the microfluidic system further comprises a second detector for detecting a said property of a said target entity or target entities, wherein said droplet dispensing unit is further configured to correlate a said target location with a said property of a said target entity or target entities detected in said second detector.

These one or more further analysis may thereby increase, for example, a probability of identifying one or more target entities, in particular a specific numerical number of target entities, in a droplet, and/or a probability of identifying one or more target entities with a specific property (e.g. a specific fluorescence level, which may be within a specific range of fluorescence levels).

In a further preferred embodiment of the microfluidic system, the droplet dispensing unit comprises a second sorting device for transferring a said droplet from a first fluidic flow path to a second fluidic flow path, said second sorting device comprising: a decoupler for decoupling a said droplet from a said first fluidic flow path; and a guide for guiding a said decoupled droplet to a said second fluidic flow path, wherein said guide comprises: a rotating unit configured to be rotated for transporting a said decoupled droplet to a said second fluidic flow path; and/or a translational unit configured to be moved in a translational direction for transporting a said decoupled droplet to a said second fluidic flow path.

The second sorting device may be used to isolate a droplet of interest based on a prior analysis. Therefore, a probability of a dispensed droplet having one or more target entities, in particular a specific numerical number of target entities, in a droplet, and/or one or more target entities with a specific property, may be increased by isolating the droplet from the first fluidic flow path.

In a further preferred embodiment of the microfluidic system, the droplet dispensing unit comprises a microfluidic channel junction comprising an input channel and a plurality of output channels, wherein said droplet dispensing unit is configured to control into which one of said plurality of output channels a said droplet is guided based on said detection via said first and/or second detectors.

Therefore, preferably, droplets which are not of interest may be put to waste. Other droplets may be sorted according to the properties of their constituents (if any) while the droplets are dispensed from the microfluidic system based on the previous analysis in the first and/or second detectors.

It will be appreciated that further one or more detectors and/or analysers may be exploited in the microfluidic system, and the dispensing of a droplet off the microfluidic system may be correlated to one or more of these further analysis in the one or more detectors and/or analysers.

In a preferred embodiment of the microfluidic system, the droplet dispensing unit comprises a pressure modulation unit for changing a pressure in a fluidic flow path of said droplet dispensing unit for controlling into which one of said plurality of output channels a said droplet is guided. By changing the pressure, for example, between different output channels, the droplets may be guided towards a specific output channel dependent on a previous analysis or detection of the droplet and dispensed from this output channel.

Alternatively or additionally, controlling the output channel from which a droplet is to be dispensed may be controlled by one or more of controlling a temperature of a droplet using a heater, using piezoelectric electrodes, using acoustic actuators, and exploiting other physical and/or mechanical properties of a droplet.

In a further preferred embodiment of the microfluidic system, a first said output channel is connected to said input channel generally in a fluidic flow path direction of said input channel, wherein a second said output channel branches off from said input channel, wherein said droplet dispensing unit further comprises a pump connected to said second output channel, wherein said pump is configured to suck off a said droplet from said input channel, and wherein said pressure modulation unit is configured to increase a pressure in said input channel in response to a said detection in said first and/or second detector to eject a said droplet via said first output channel.

Once a droplet of interest has been detected, the pressure may be increased in the input channel, such that the droplet is provided to the first output channel, rather than being sucked off by the pump into the second output channel.

It will be appreciated that alternatively, the pressure in the input channel may generally be above a threshold such that a droplet is, without a pressure change in the input channel, provided to the first output channel. Once a droplet of interest has been detected, the pressure in the input channel may be decreased such that the target droplet is sucked into the second output channel by the pump.

In a preferred embodiment, the microfluidic system further comprises one or more droplet holding regions, wherein a said holding region is arranged between said sorting device and said droplet dispensing unit, and wherein a said holding region is configured to control a flow of a said sorted droplet to said droplet dispensing unit. This embodiment allows for a more precise and accurate control of droplet flow into the droplet dispensing unit.

In a further preferred embodiment, the microfluidic system further comprises a plurality of sensors for detecting a said droplet at different locations of said microfluidic system (at different points in time) to determine a velocity of said droplet in said microfluidic system, and wherein said sorting device is configured to sort said droplet dependent on an outcome of said velocity determination. This may be particularly advantageous as the location of the droplet(s) in the microfluidic system may be determined and/or predicted, which allows for an improved control of sorting the droplet(s) in the sorting device.

In a further related aspect of the present invention, there is provided a microfluidic chip comprising: a droplet generation region for generating microdroplets which contain one or more biological entities; a droplet incubator and/or storage region for incubating and/or storing said biological entities; a droplet sorting region for sorting said microdroplets based on one or more properties of said biological entities; and a droplet dispensing region for dispensing said sorted microdroplets; and wherein said droplet generation region, said droplet incubator and/or storage region, said droplet sorting region and said droplet dispensing region are incorporated on a single chip design of said microfluidic chip.

The microfluidic chip ensures sterility, ease of use and allows for significant cost-savings as the generator, incubator, sorting chip and dispenser are incorporated into a single microfluidic chip.

In a preferred embodiment, the microfluidic chip comprises a microfluidic flow path diversion unit for changing a microfluidic flow path of a said microdroplet between said regions; and a control unit comprising a first processor for controlling said microfluidic flow path diversion unit. This may be preferable since a certain part or parts of the microfluidic chip, for example the incubation region, may be omitted, so that it may not be used for processing a particular droplet or droplets.

Various valves may be provided on the microfluidic chip which allow for controlling the flow or rate of flow of microdroplets thought the different regions of the microfluidic chip.

In a preferred embodiment, the microfluidic chip further comprises a heater for locally heating droplets at the droplet incubator and/or storage region (and/or at other specific regions), and further comprising a second processor for controlling said heater. The first and second processor may be a single processor. Embodiments may therefore advantageously allow for heating droplets and their constituents only at certain locations or regions of the microfluidic chip, such that heating of droplets in other regions of the microfluidic chip may be avoided.

In a further preferred embodiment, the microfluidic chip further comprises a cooler for locally cooling droplets at the droplet incubator and/or storage region (and/or other specific regions), and further comprising a third processor for controlling said cooler. The first, second and/or third processors may be a single processor. Embodiments may therefore advantageously allow for cooling droplets and their constituents only at certain locations or regions of the microfluidic chip, such that cooling of droplets in other regions of the microfluidic chip may be avoided.

Embodiments which may provide heating (and optionally cooling) may allow for example for polymerase chain reaction to be performed at one or more specific regions of the microfluidic chip.

It will be appreciated that preferred embodiments described above with regard to the microfluidic system, the droplet sorting or dispensing device, the droplet dispenser, the microfluidic device, the microfluidic cartridge, the microdroplet processing system and the instrument for microdroplet-based processing of biological entities may also be implemented as preferred embodiments in the microfluidic chip.

Multi-Mode Operation

In another aspect the invention provides an instrument for microfluidic droplet-based processing of biological entities, the instrument comprising: a droplet generation system to generate one or more water-in-oil emulsions of droplets comprising biological entities; a droplet processing system to process said droplets; and a droplet dispensing system to dispense processed said droplets into one or more reservoirs; wherein said droplet processing system is configurable for multiple different modes of operation including at least a monoclonality mode of operation and an assay mode of operation.

In embodiments the droplet processing system includes at least a droplet sort function/unit and the monoclonality mode of operation comprises sorting droplets based on occupancy of the droplet by the biological entities. The assay mode of operation includes incubating the droplets, preferably but not essentially in a droplet incubation unit, prior to sorting. The sorting may then be based on a product of the biological entities during the incubation. The droplet processing system may further comprise at least one droplet fusion unit and the modes of operation may then include a fusion assay mode, sorting based upon the result of a combination of biological entities in one set of droplets with material, for example other biological entities, in a second set of droplets. In embodiments the droplet processing system is embodied in one or more interchangeable or modular cartridges—that is, for example, a different cartridge may be provided for each of the different modes of operation or, alternatively, a modular cartridge may be employed in which different droplet processing functions—such as a sort function, incubation function, dispensing function and the like—may selectively be assembled on a cartridge substrate.

In more detail, a monoclonality mode of operation may comprise encapsulating the biological entities, typically cells, within droplets, preferably in a manner which is biased towards a majority of empty droplets. Those droplets which are then identified in the sorting unit as being occupied by a single cell are selectively directed to the droplet dispensing unit, where they are processed and dispensed. In embodiments a single droplet may be dispensed into an individual well or reservoir, but it can also be acceptable to dispense two or more droplets into a reservoir or well. For example if the entities or cells are going to be re-injected for further processing then a well/reservoir may hold a larger number of droplets.

In an assay mode it can be acceptable to encapsulate more than one entity/cell per droplet, for example two or three cells per droplet. In embodiments these are then provided to an incubation chamber where they are warmed and metabolise to produce a product such as a protein or the like. Typically the product interacts with one or more reagents within the droplet creating a measurable signal, for example a fluorescence signal, and this may then be used to sort the droplets, for example to collect and dispense the best producers. Optionally a sorting unit may be provided prior to the incubation region, in particular to remove empty droplets before incubation. This helps to reduce the volume of the incubation chamber and is particularly advantageous where the droplet generation/entity encapsulation results in a large percentage of empty droplets—depending upon the process used 90% or more of droplets may be empty.

In another assay mode, which may be termed a stability assay mode, a similar incubation, selection and dispensing process may be employed, but with the aim of identifying a subgroup of the initial population. Such a subgroup may be a subgroup which exhibits optimum production, typically of a protein, for example for drug fabrication. The optimum production need not necessarily be the maximum production but may be, for example, consistent production (production which is maintained over a period rather than decaying with time), or production which is maintained over a (wide) range of environmental conditions. Thus embodiments of such a stability assay may be employed to identify those entities which are stable producers, for example to select producers for a production process such as a fermentation process, or for quality control of a production process. In embodiments an entity may be encapsulated with one or more reagents within a droplet and then incubated, afterwards looking for a measurable signal, such as a fluorescence signal, which may then be used to differentiate a target sub-population of the entities for dispensing and collection in one or more reservoirs.

In a further aspect, in a fusion mode of operation a typical procedure involves generating two sets of droplets, at least one encapsulating biological entities; these may be generated in advance and provided in respective reservoirs or may be generated, for example, on-cartridge. The fusion assay may then comprise droplet fusion, incubation, sorting, and dispensing. Optionally pre-sorting may be employed, prior to incubation as previously described and/or after droplet fusion. A fusion assay may be employed, for example, for a toxicological study, environmental study, metagenomic study, a study of drug uptake, or the like. For example in the latter case a drug may be provided in one set of microdroplets at a known concentration and the concentration of the drug may then be measured after incubation (either remotely or by taking an aliquot), to determine a change in concentration of the drug from which drug uptake may be inferred.

For each of the above described modes of operation, in embodiments the dispensing unit may also provide an additional selection step—that is the droplet dispensing the system may comprise a combined droplet sorting and dispensing stage.

BRIEF DESCRIPTION OF THE DRAWINGS

These and other aspects of the invention will now be further described, by way of example only, with reference to the accompanying figures in which.

DETAILED DESCRIPTION OF PREFERRED EMBODIMENTS

Figure 1:
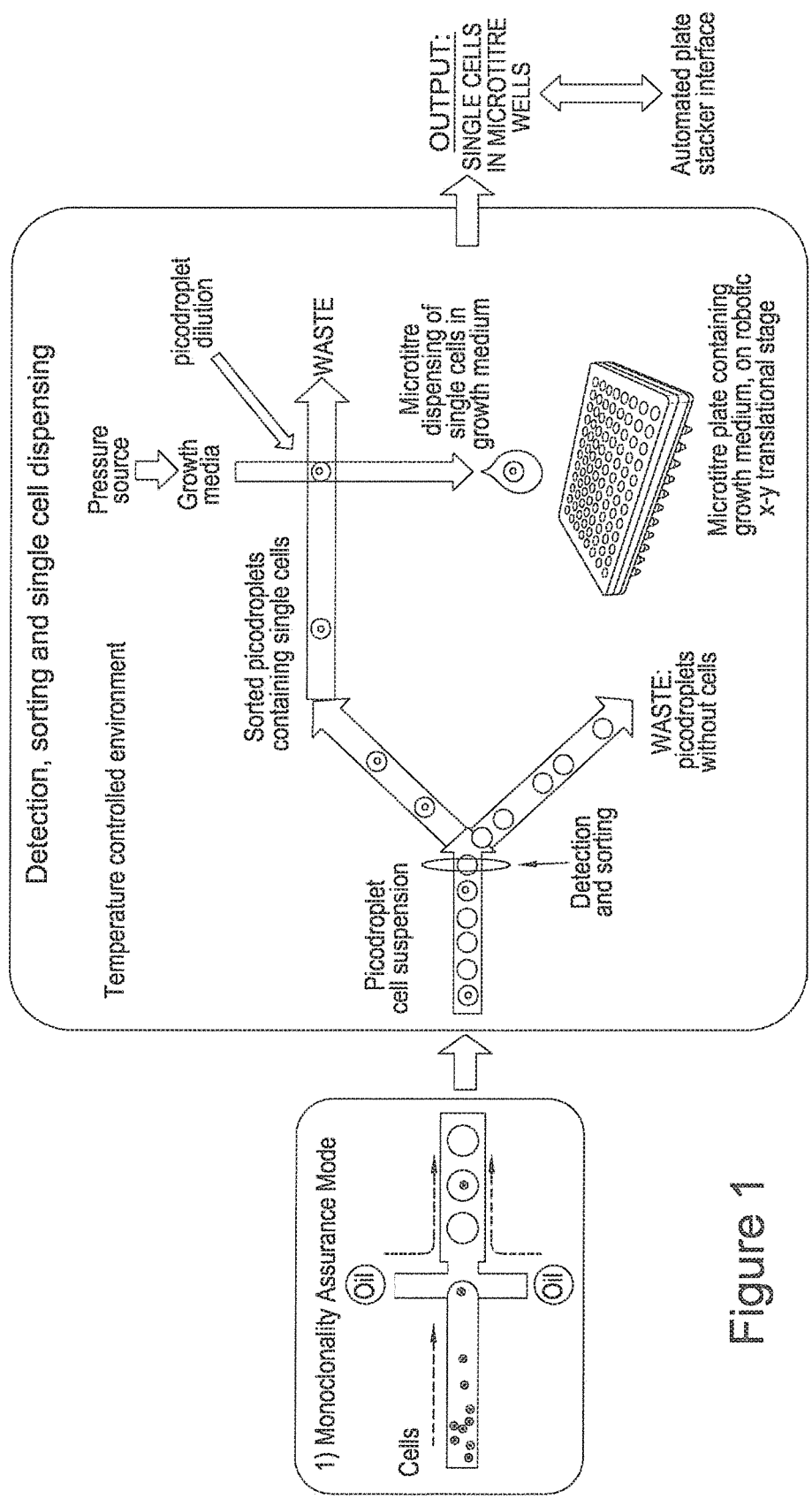
FIG. 1 shows a schematic illustration of droplet detection, sorting and dispensing according to embodiments of the present invention.

FIG. 1 shows a schematic illustration of a first example of droplet detection, sorting and dispensing according to embodiments described herein. This mode is termed, in this example, monoclonality assurance mode.

In this example, multiple cells are provided in a fluid, in this example water, optionally including a growth medium. In the first step, individual droplets are formed from the fluid. As outlined above, this may be achieved by using, for example, T-junctions, Y-junctions, flow focussing devices, or other devices. The droplets which have been generated are, in this example, transported in a fluid of oil.

The individual droplets, which may or may not contain one or more cells, are then guided through the microfluidic device in an oil emulsion.

In this example, the picodroplet cell suspension, i.e. the droplets in the oil emulsion, are guided towards a detection and sorting device. Whether or not a single droplet contains one or more cells may be detected in the analyser, based on one or more of electrical, optical, thermal, acoustic, mechanical, temporal, spatial, and other physical characteristics of the droplets. Based on the analysis in the analyser, i.e. the determination as to whether a single droplet contains one or more target cells, the droplet may be sorted in the droplet sorting device. In this example, picodroplets which do not contain one or more cells are put to waste. Furthermore, droplets which contain, in this example, the single cell of interest are guided towards a decoupler of the microfluidic system.

Droplets which contain one or more cells of interest are then extracted from the first fluidic flow path and transferred into a second fluidic flow path. In this example, the target droplets are extracted from the first fluidic flow path in a growth media fluid. A droplet which contains a target cell, whereby the droplet is incorporated in the growth media fluid, is then dispensed into a microtitre plate via pressurised fluid ejection. A pressure source is, in this example, attached to the flow path at which the growth media fluid is injected. The picodroplets may thereby be diluted. A robotic xy translational stage is provided in this example in order to dispense droplets into different wells of the microtitre plate.

The droplet detecting, sorting and cell dispensing are, in this example, performed in a temperature controlled environment.

In this example, picodroplets which contain a single cell and which are not to be disposed into the microtitre plate, are guided in the first fluidic flow path to waste.

As outlined above, the probability for finding a single cell in a single droplet which is disposed into the microtitre plate, may be higher than 99.997%.

In the example of FIG. 1, an automated plate stacker interface may be provided, in order to stack various microtitre plates on top of each other.

In some preferred implementations of the system of FIG. 1, and similarly of the later described systems, an imaging device such as a camera is provided at or close to the point at which the droplets are dispended (into the microtitre plate). The imaging device may be used to image a droplet to determine whether the droplet contains just a single cell (or other biological entity), or alternatively two or more cells, or no cells. In other approaches optical detection of scatter from a droplet may be detected for this purpose. Such an optical system may then be used as a tool to monitor monoclonality, more particularly in conjunction with a control system to identify and log when a well does not contain just a single cell (or vice-versa), for example so that the system may then flag an error for the identified well.

Figure 2:
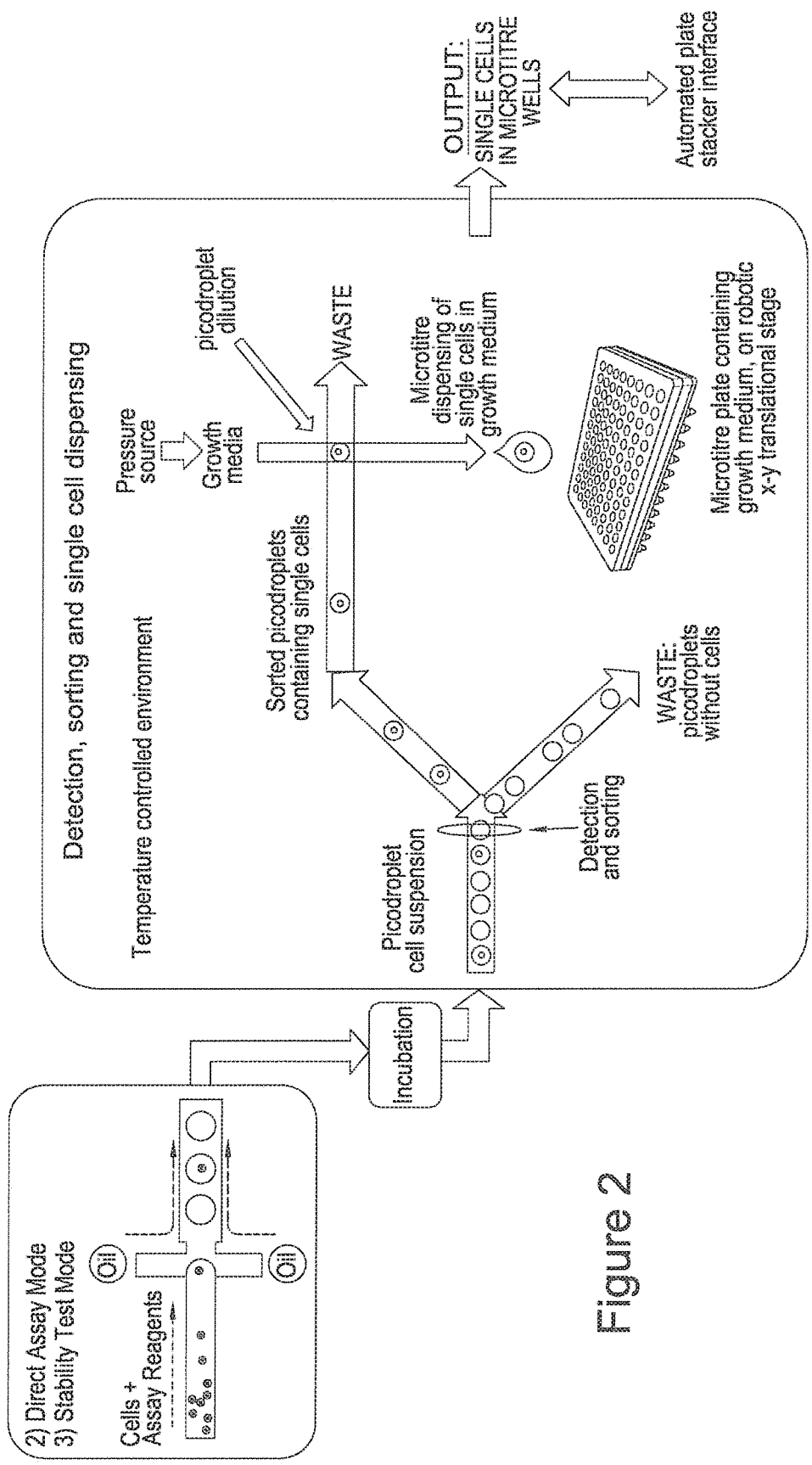
FIG. 2 shows a schematic illustration of a further example of droplet detection, sorting and dispensing according to embodiments of the present invention.

FIG. 2 shows a schematic illustration of a further example of droplet detection, sorting and dispensing according to embodiments described herein. Two different modes of operation, a direct assay mode, as well as a stability test mode are displayed.

In this example, cells are provided in a fluid together with assay reagents. Individual droplets are then formed from the fluid as outlined in the example shown in FIG. 1.

Droplets which have been prepared from the fluid containing cells and assay reagents, are then guided into an incubator. The incubator may be used to grow and/or maintain the cells in the droplets. As outlined above, the incubator may comprise a stability test unit which allows for performing stability tests on the cells during the incubation. Performing a stability test on a cell in a single droplet allows for sorting only viable cells during the detection and sorting steps in the analyser and droplet sorting device, which have not degraded or died during the stability test.

Further steps of determining the content of a droplet, sorting the droplet based on the determination, and a potential extraction of a droplet of interest in the decoupler are performed as outlined with regard to the schematic illustration of FIG. 1.

Figure 3:
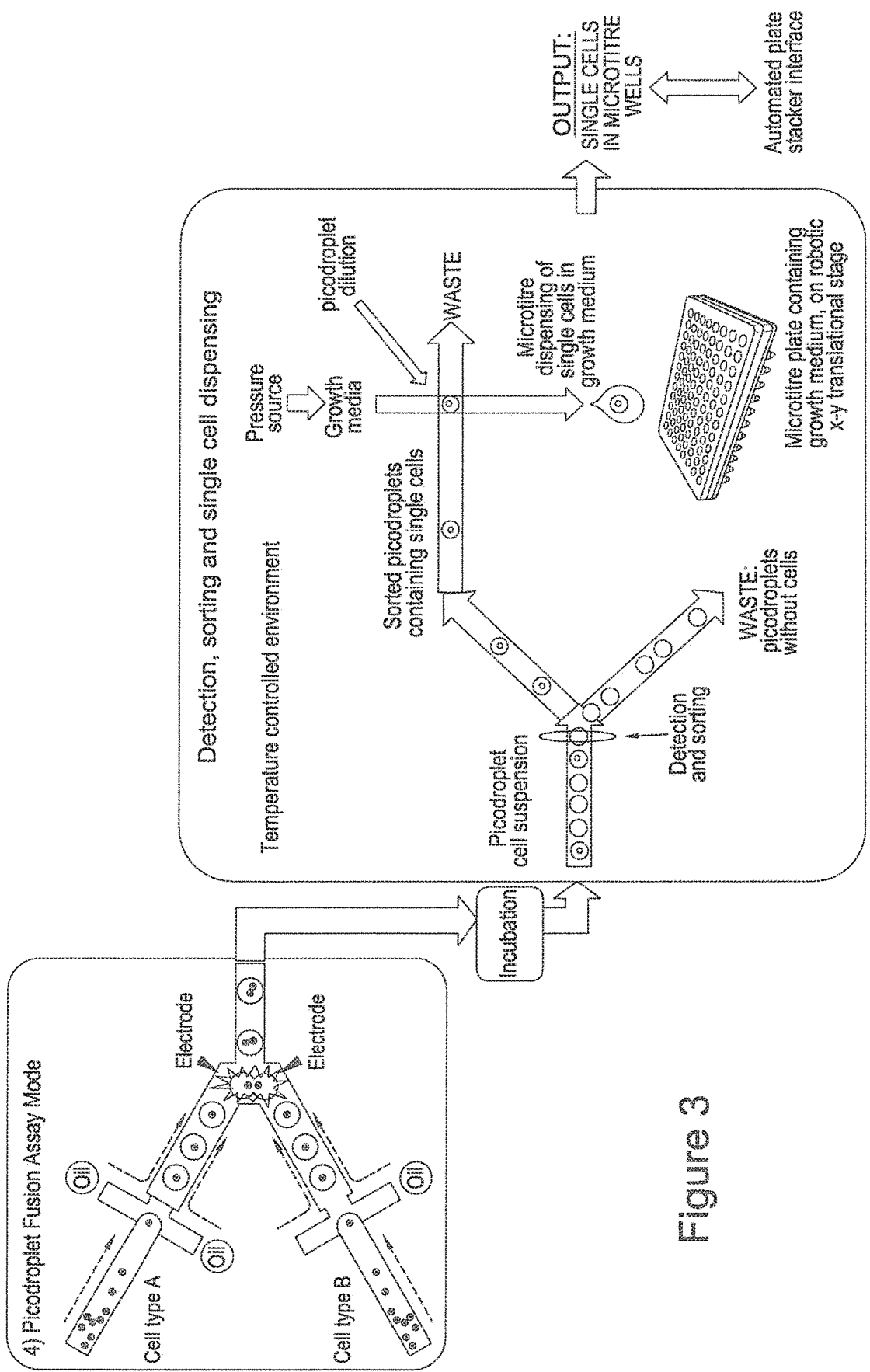
FIG. 3 shows a schematic illustration of a further example of droplet detection, sorting and dispensing according to embodiments of the present invention.

FIG. 3 shows a schematic illustration of a further example of droplet detection, sorting and dispensing according to embodiments described herein. This mode is termed, in this example, picodroplet fusion assay mode.

In this example a picodroplet fusion assay mode is illustrated. The first cell type A is provided in a first fluid. Individual droplets are then formed from this first fluid. A second cell type B is provided in a second fluid, from which individual droplets are formed. Droplets which have been prepared from the first fluid, as well as droplets which have been prepared from the second fluid, are guided towards a fusion device (electrodes in FIG. 3). In this example, two droplets from the first and second fluids, respectively, are prepared by electro-coalescence. The fused droplets may then be processed further as shown in the schematic illustrations of FIG. 1 and/or FIG. 2.

As outlined above, the droplet fusion device may be placed, for example, behind the analyser and droplet sorting device in a fluid flow direction of the microfluidic system. Such a configuration may allow for fusing droplets in the droplet fusion device only for droplets which have been determined to contain, in this example, cells which are of interest for growth and/or further analysis and processing.

Figure 4A:
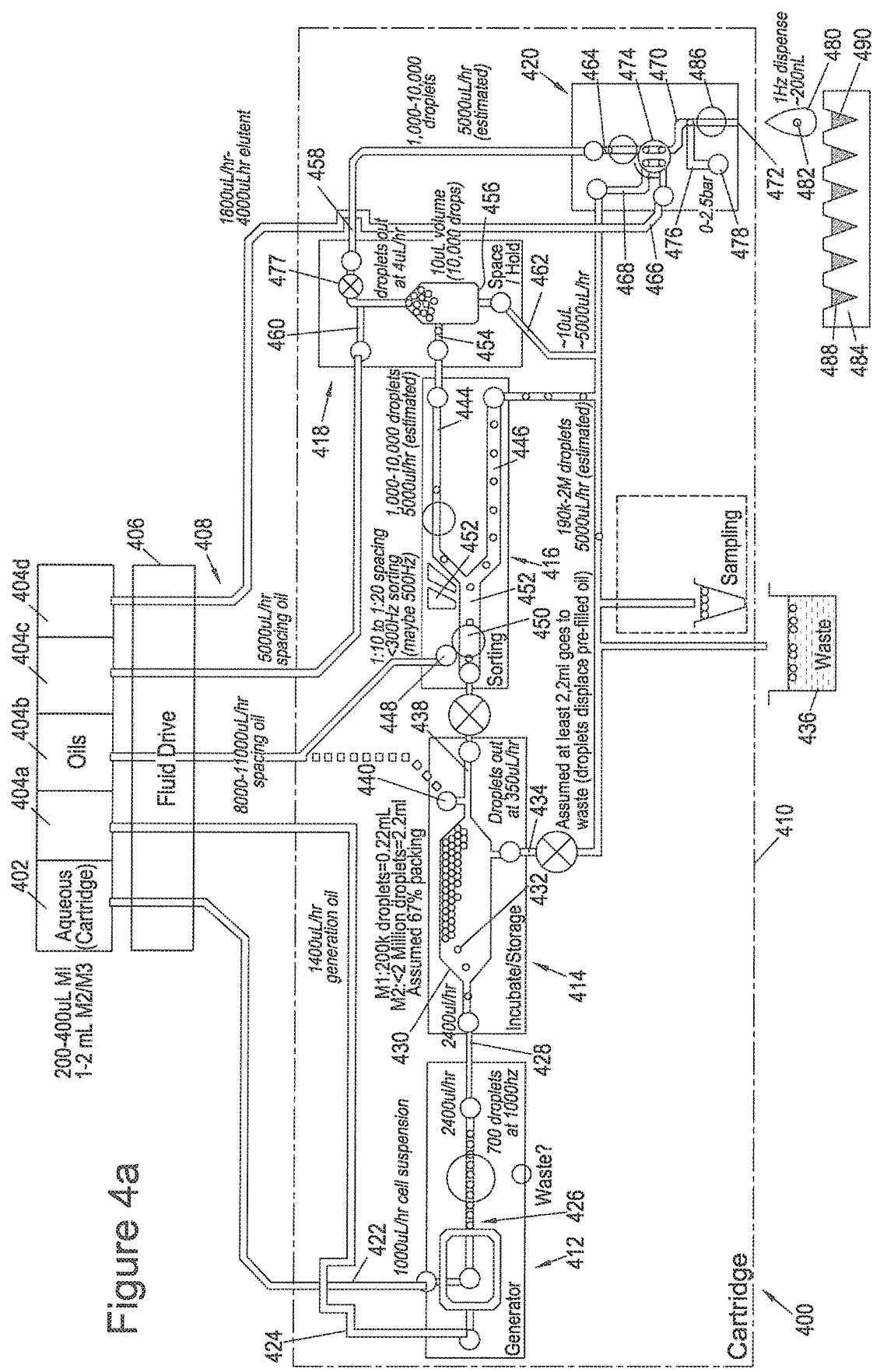
FIGS. 4a and b show schematic illustrations of a microfluidic cartridge according to embodiments of the present invention.
Figure 10A:
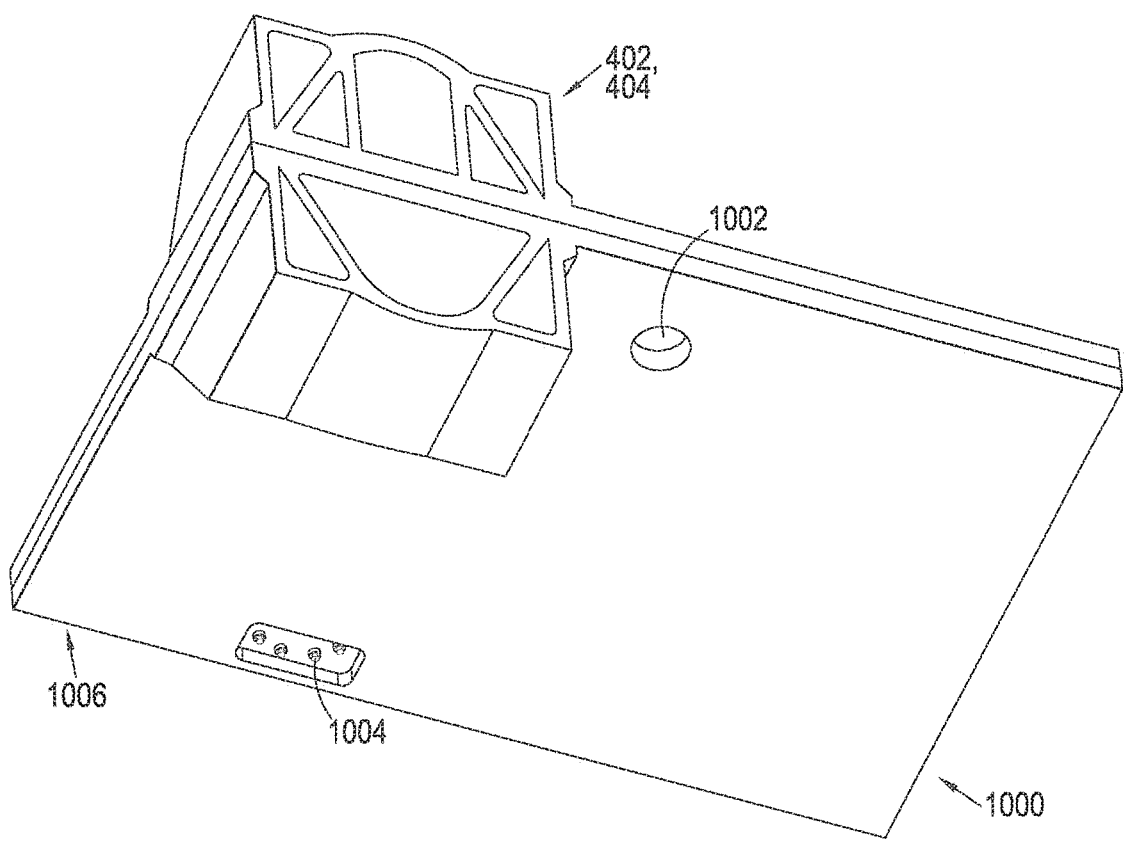
FIGS. 10a and 10b show views of further microfluidic cartridges according to embodiments of the present invention.

Referring now to FIG. 4a this shows a block diagram of an embodiment of a microdroplet processing system/instrument 400 incorporating a (disposable) microfluidic cartridge 410 according to an embodiment of the invention. The instrument 400 has a reservoir 402 holding an aqueous medium, generally including growth media, within which biological entities such as mammalian cells, bacteria or the like are held for processing. A set of reservoirs 404*a-d* hold oil for providing an emulsion at various stages of the system. Although reservoirs 402, 404 are shown as part of the instrument rather than part of the cartridge, in other embodiments (as shown in FIG. 10*a* later) they may be part of the cartridge; depending upon the cartridge function, for example whether it is to be used for a fusion or functional assay, there may be more than one aqueous reservoir 402. The fluids from reservoirs 402, 404 are pumped by respective pumps in FIG. 4*a* illustrated by fluid drive module 406, which again may be integrated with the cartridge. A set of fluid flow lines 408 connect to respective ports on the cartridge when the cartridge is inserted into the instrument, as also illustrated later with reference to FIG. 12.

The illustrated cartridge 410 comprises a droplet generation region 412, a droplet incubation/storage region 414, a droplet sorting region 416, a flow buffer region 418, and a droplet dispenser 420. In embodiments of the cartridge each of these regions is modular and an emulsion flow processing configuration may be selected by selecting modules to attach to a cartridge base or holder so that the selected modules interface with one another to perform the desired function for a particular cartridge.

In FIG. 4*a* the smaller circular regions represent inlet/outlet ports for the droplet processing regions which, depending upon the cartridge configuration may represent on-cartridge or off-cartridge connections; the larger circular regions represent optical droplet sensing regions, and the crossed circles represent valves.

In embodiments the droplet generation module or region 412 of the cartridge comprises an aqueous sample inlet 422 and an oil inlet 424 for generating the emulsion. Flows of these liquids are provided to a flow focus junction 426 where the emulsion is generated and provided to an output channel 428 of the region. By way of example, to provide some illustrative numbers, the generation oil may have a flow rate of 1400 pl per hour, the sample, for example a cell suspension, may have a flow rate of 1000 pl per hour and the water-in-oil emulsion in the output channel may have a flow rate of 2400 pl per hour comprising 700 picolitre droplets at 1000 Hz.

The emulsion (which may alternatively be created off-cartridge and added to a reservoir) is then in this example provided to the incubate/storage region 414. This comprises a storage chamber 430 within which the individual droplets 432 float upwards whilst excess oil flows to waste through channel 434 (via a valve) into reservoir 436 from which, potentially, the oil may be recycled. In embodiments, the oil comprises fluorous oil, which is particularly suitable for trapping oxygen which allows for example for enhanced growth of, e.g. biological entities, such as cells, in the droplets while being stored in the chamber 430. The chamber 430 may therefore be filled up with fluorous oil above a threshold (e.g. 50% of the volume of the chamber 430, or more), such that enough oxygen may be provided to the entities in the droplets over a certain period of time. In embodiments the instrument in which the cartridge is located includes a heating device such as a heater plate and/or a cooling device such as a Peltier effect device adjacent the incubation chamber 430, preferably together with a temperature sensor for temperature control. In this way the chamber may be heated for a controlled period to incubate the contents of the droplets and then cooled to substantially inhibit the incubation. The incubation chamber has an outlet channel 438 with an optional side channel 440 to receive spacing oil to space the droplets in the emulsion in the outlet as they are fed out from chamber 430. Continuing the previous numeric example around the 200,000 droplets can be stored in a volume of 0.22 ml and a little under 2,000,000 million droplets in a volume of around 2.2 ml (assuming 67% packing), and thus around 2.2 ml of oil may go to waste (since the droplets displaced the oil previously filling the chamber). The output channel 438 from the incubation region may have a flow rate of around 350 pl per hour; spacing oil may be added at port 440 or in the subsequent sorting region (see later) at a rate of around 8,000-11,000 pl per hour.

Sorting region 416 as an input channel 442 in this embodiment coupled to the output channel 438 of the incubation region, and a pair of output channels 444, 446, channel 444 containing the desired droplets with their load of selected, target analyte (entity or entities). Channel 446 runs to waste reservoir 436. Optionally an inlet 448 is provided for adding spacing oil to the flow into the sorting region. The sorting region includes a region 450 where the droplet contents are (optically) interrogated by the instrument holding the cartridge, which then drives electrodes 452 to selectively direct droplets into either channel 444 or channel 446 (connections to electrodes 452 are not shown in FIG. 4a, for simplicity). Continuing the previous numeric example the mark:space ratio of droplets in the input emulsion for the sorting region 416 may be of order 1:10 to 1:20 and the droplets may enter the sorting region at the rate of a few 100 Hz. The flow rate in channel 444 may be of order 5,000 pl per hour, containing between 1,000 and 10,00 droplets; the flow rate of emulsion in channel 446 may be substantially the same but this emulsion may comprise of order 190,000-2,000,000 droplets (per hour).

The 'target' output channel 444 of the sorting region is coupled to an input channel 454 of space/hold or 'flow buffer' region 418. This comprises a chamber 456, typically somewhat smaller than the incubation chamber 430, within which droplets are temporarily held (for example floating at the top of the chamber) prior to release into output channel 458. In embodiments, the oil comprises fluorous oil, which is particularly suitable for trapping oxygen which allows for example for enhanced growth of, e.g. biological entities, such as cells, in the droplets while being stored in the chamber 456. The chamber 456 may therefore be filled up with fluorous oil above a threshold (e.g. 50% of the volume of the chamber 456, or more), such that enough oxygen may be provided to the entities in the droplets over a certain period of time. The release from chamber 456 is facilitated by adding spacing oil via input channel 460. In a similar manner to the incubation region, the flow buffer region also includes an output channel 462 to waste reservoir 436. By way of numeric example, a 10 ml volume of chamber 456 may hold 10,000 droplets. The output flow rate in channel 458 may be of order 4 pl per hour; the spacing oil in channel 460 may flow at around 5,000 pl per hour; the waste in channel 462 may flow at a variable rate of, for example, 10-5,000 pl per hour.

In the illustrated embodiment the flow buffer region 418 output channel 458 provides an input via channel 464 to droplet dispenser region 420. In the illustrated embodiment of the dispenser channel 466 provides a second input to the dispenser carrying eluent, that is oil used to/for extraction and ejection of target droplets.

The dispenser has a first output channel 468 which again flows to waste, and a second output channel 470 which provides an outlet 472 for the dispenser for ejecting selected droplets for collection in a reservoir. A further channel 476 is coupled to an inlet 478, in this example to receive compressed air at pressure in the range of, for example, 0-2.5 bar. In this way a pressure pulse can be applied to the emulsion flowing in the output channel 470 (after closing valve 477) to eject a slug of emulsion 480 containing a selected, target droplet 482 for collection in a well of a multi-well reservoir 484. In the illustrated embodiment the dispenser 420 has a rotary valve 474 which can be used to selectively direct a droplet into a fluid flow linking with the dispenser output channel 470 or into a fluid flow linking with the waste channel 468.

Optionally the dispenser 420 may comprise one or more droplet sensing regions for 486. These may be used to identify when a droplet is present in the flow and to control the timing of the droplet ejection accordingly in order to eject emulsion slug 480. Additionally or alternatively one or more of these seeing regions may be employed to sense the contents of a target droplet, and in embodiments this sensing may be used to apply a further level of selection to the ejected droplets, for example to provide a further guarantee of monoclonality of the contents of droplet 482 or to provide some father selectivity over the droplet contents or over a number or numeric range of entities within droplet 482.

In embodiments the multi-well plate 484 may comprise a plurality of wells 488 within which optionally an aqueous (growth) medium 490 may be provided. In embodiments multi-well plate 484 is moved, for example by an X-Y stage (not shown) so that each well receives just one slug of emulsion containing just a single droplet. Moreover in embodiments the instrument controlling the system of FIG. 4a senses a property of the droplet, more particularly the contents of a droplet either in the sorter (or if the droplet is not easily tracked during its passage through the buffer region, later in the dispenser). Thus a log may be generated and stored defining one or more properties of each droplet in its respective well, for example its fluorescence or the like. In this way a few or individual single entitles with a property or properties of interest can be selected for further study or use, for example for analysis, antibody generation, fermentation or the like.

Various sensors may be employed, for example in the regions 414, 416 and 420 of the microdroplet processing system/instrument 400, which allow for detection of droplets. These sensors may be optical sensors and/or electrical sensors. Electrical sensors may make use of the fact that if a cell in a droplet is present, the insulating cell has an effect on the electrical property of the droplet, such that capacitance measurements allow for detecting as to whether a droplet storing a cell is present or not. Using capacitance measurements, the size of a droplet may further be determined. The skilled person will be familiar with alternative methods and techniques for detecting a droplet and/or the droplets constituents.

The sensors may be used to count the droplets, and by providing a plurality of sensors in sequence, the velocity of the droplets flowing through the processing system/instrument may be determined. This allows for example for activating sorting of a droplet at an appropriate time. This may make the droplet processing system or microfluidic chip more efficient since the units which allow for droplet sorting may need to be activated at certain times only.

In some examples, a further sensor is provided behind a sorting junction in a flow direction. The further sensor may be used to double-check whether a droplet has been sorted into the correct flow path/channel, by comparing a detection of a droplet with the further sensor to detection data from sensors upstream from the sorting junction and based on the determined velocity data. If a droplet has not been sorted correctly, further action may be taken downstream from the sorting junction by sorting the earlier sorted droplet further between a plurality of flow paths/channels.

Figure 4B:
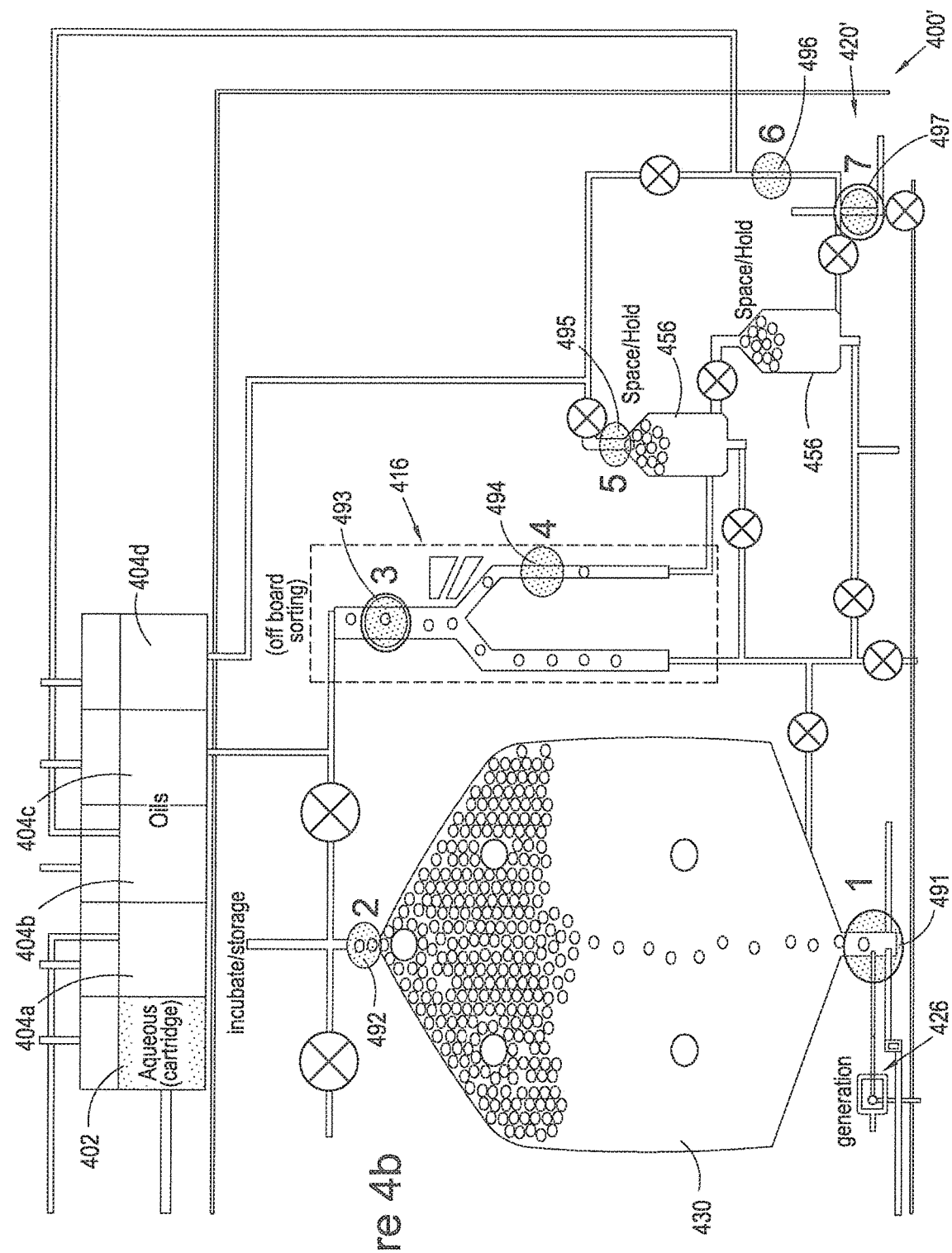

Referring now to FIG. 4*b*, this shows another embodiment of a microdroplet processing system/instrument 400', in which like elements to those previously described are indicated by like reference numerals. The arrangement of FIG. 4*b* may be implemented partly or even wholly separately to the previously described cartridge, for example on linked modules within the instrument. On preferred implementation of the arrangement of FIG. 4*b* is as a 'semi-modular' cartridge, with off-board droplet generation and off-board droplet sorting, but on-board droplet incubation/storage and dispensing. As previously, crossed circles indicate valves; in the variant of FIG. 4*b* two flow buffer regions are shown. The skilled person will appreciate that multiple different systems may be assembled with different functionalities according to requirements.

Figure 5A:
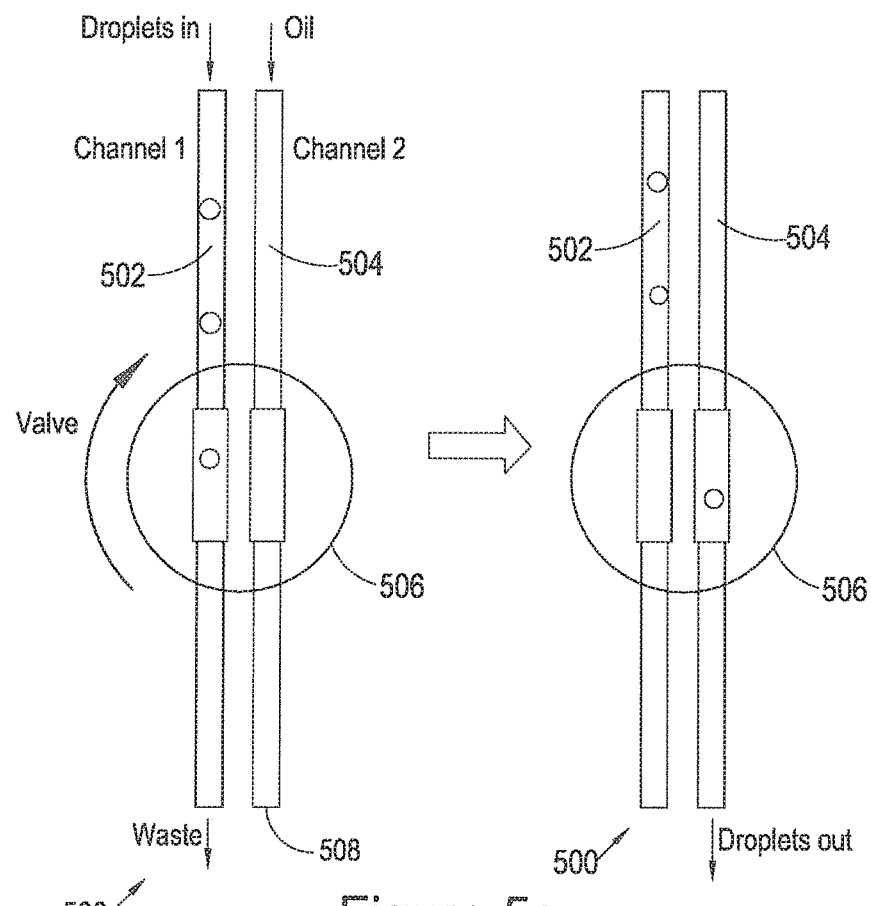
FIGS. 5a and 5b show schematic illustrations of a decoupler and control unit according to embodiments of the present invention.

Some of the optical systems used in preferred embodiments of the instrument will now be described with reference to FIG. 4*b*; similar optical systems may be used with the arrangement of FIG. 4*a* and it will be appreciated that, depending upon the application, not all of the describable systems will be needed. Thus in the arrangement of FIG. 4*b* a first optical sensing region 491 is used by an optical system for sizing the droplets; a second optical sensing region 492 is used for optical diagnostic purposes. A third optical sensing region 493 is used for optical cell detection and sorting (for example by imaging cells within droplets), and a fourth optical sensing region 494 may be used for post-sort diagnostics. Optical sensing region 495 may similarly be used for diagnostic purposes, optical sensing region 496 may be used for timing purposes (for example to establish droplet position/speed/time to the dispenser), and droplet optical sensing region 497 may be used for droplet contents (cell) detection, for example for use in (selective) dispensing. The dispensing region 420' in the instrument of FIG. 4*b* may comprise a dispenser of the type described with reference to FIG. 8, below. FIG. 5*a* shows a schematic illustration of a decoupler 500 according to embodiments described herein, whereby a droplet may be extracted from a first fluid flow path (channel) 502 by transferring the droplet from the first fluid flow path into a second fluid flow path (channel) 504.

In this example, individual droplets are guided in first channel 502 in a water-in-oil emulsion towards the decoupler. Once a droplet of interest has entered the decoupler, a rotating unit 506 of the decoupler may be rotated such that the droplet of interest is transferred from the first channel into the second channel 504 of the device. Oil flowing in the second channel may then guide the droplet to an outlet 508 of the second channel. Once the droplet is in the second channel 504 of the device it is decoupled from the first channel and pressure is then preferably applied to the second channel to eject the selected droplet from outlet 508.

The decoupler may be used, for example on a microfluidic chip, to isolate a volume of fluid (slug of emulsion) containing the picodroplet or other volume of interest (for example cell, bacteria, and others), and translate this volume of fluid from the first fluidic flow path to the second fluidic flow path, wherefrom the droplet may subsequently be dispensed off the microfluidic chip.

The decoupler with, in this example, the rotating unit allows for accurate capture and isolation of the fluidic volume without major disruption to the first fluid flow path within the microfluidic channel network. The decoupler further allows decoupling of the off-chip dispensing mechanism, ensuring accurate and rapid expulsion of the isolated fluid volume off the chip. In this example, the rotating unit of the decoupler may operate at rates of up to 5 Hz or greater (in embodiments limited by the rate of step movement of the microtitre plate).

A decoupler as show in FIG. 5*a* may form part of a droplet dispenser. In one approach, as illustrated, a droplet selected for ejection may be transferred from channel 502 to channel 504 and then pressure such as air pressure applied to channel 504 to eject the droplet (in a slug of emulsion). If a droplet is not wanted/not to be ejected it may be left in channel 502, which runs to waste. Alternatively channel 504 may be run to waste and unwanted droplets transferred from channel 503 to channel 504; then droplets for ejection may be ejected from an open of channel 502, again by air pressure or the like.

Figure 5B:
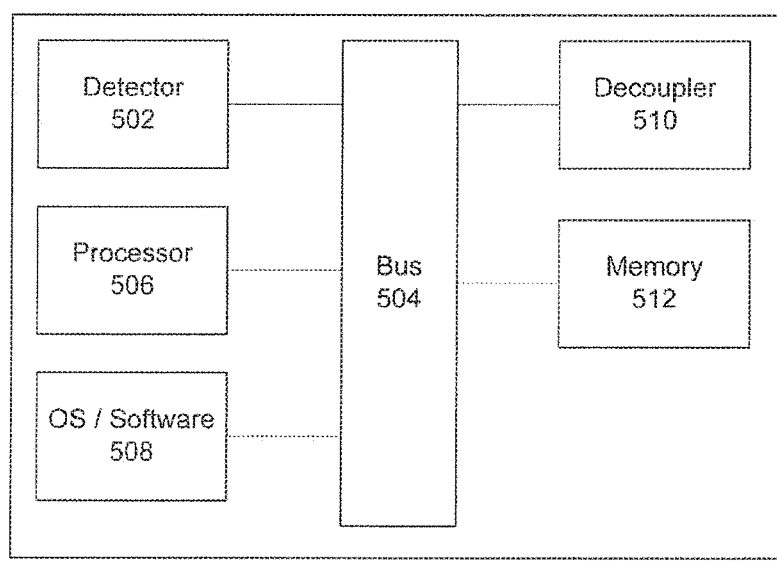

FIG. 5*b* shows a block diagram of an example control unit for the decoupler. The control unit 500 comprises, in this example, a detector 502, which may be used to detect the contents of a droplet and their physical properties. The detector 502 as well as other units of the control unit 500, are connected to each other via bus 504.

The processor 506 is configured to process the signal obtained from detector 502. An operating system/software 508 is provided in the control unit 500, which may be applied to the signal processed in processor 506 and obtained via detector 502, in order to determine the constituents and their physical properties of, in this example, cells in a droplet. The operating system/software 508 may be stored in memory 512.

Depending on the outcome of the signal provided from detector 502 to processor 506, a signal may be provided to the decoupler 510. This signal is used to control, in this example, the rotating unit of the decoupler 510, to thereby maintain a droplet in the first fluidic flow path, or to transfer the droplet from the first fluidic flow path to the second fluidic flow path.

Any information regarding, for example, the constituents of analysed droplets, the number of droplets which have been transferred from the first fluidic flow path to the second fluidic flow path, and other information may be stored in memory, which may be integral to memory 512.

Figure 6:
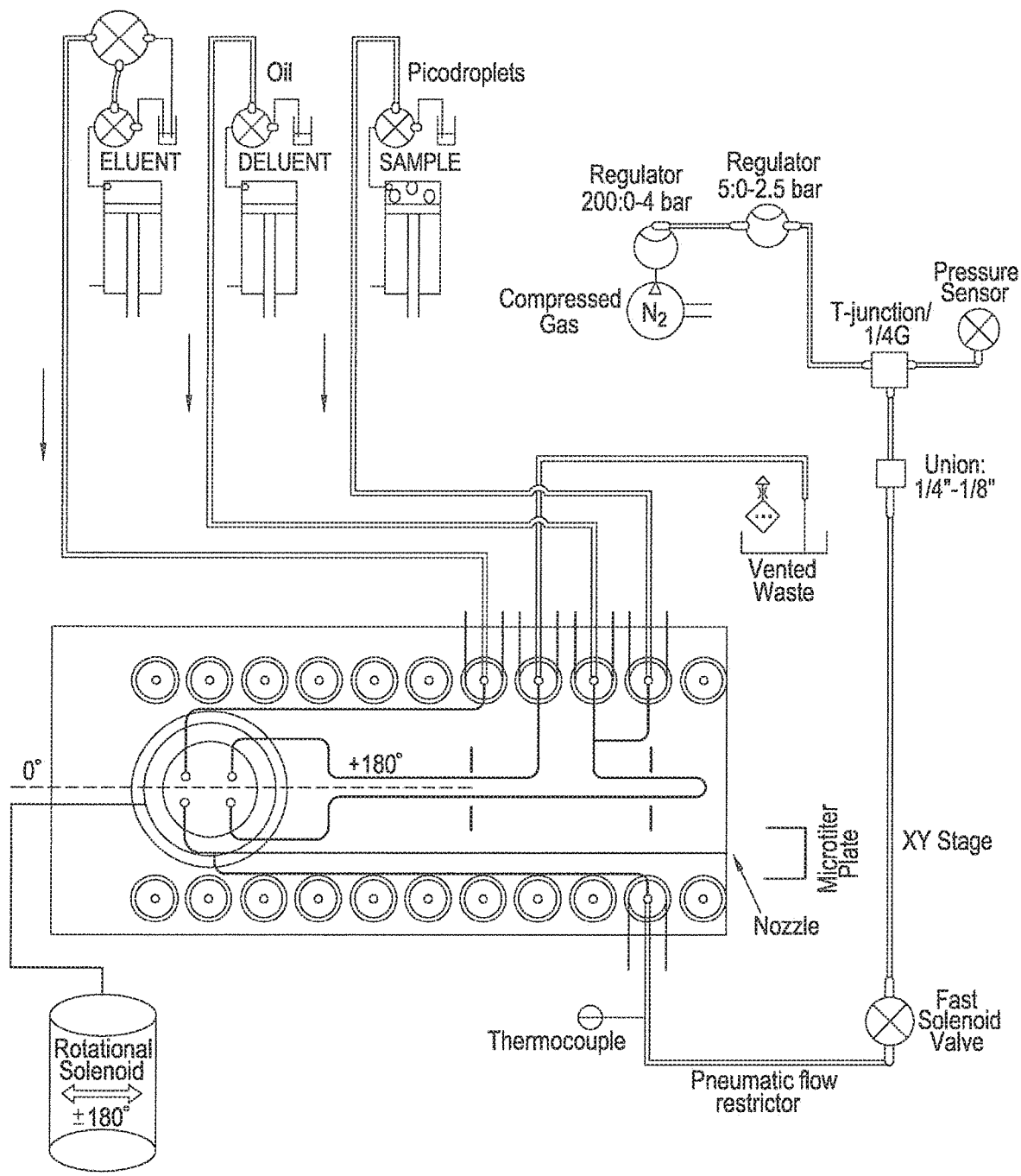
FIG. 6 shows a schematic illustration of fluid flows and a decoupler according to embodiments of the present invention.

FIG. 6 shows a schematic illustration of example fluid flows and a decoupler according to embodiments described herein. As can be seen, the samples of interest are provided in a fluid which may be stored in a container, for example on a microfluidic device. Picodroplets may be prepared from the fluid generally as outlined above. In this example, further containers are provided for an eluent and a diluent. An oil reservoir may allow for an oil flow to guide water droplets containing one or more entities through the device.

In this example, each of the eluent container, diluent (oil) container and the sample fluid container are connected to different inputs of the decoupler by microfluidic channels. Once a droplet enters the decoupler at an input, the droplet may be guided via the decoupler channel network to, in this example, a rotating unit. The droplet may then be transferred from one channel to another channel by rotating the rotating unit.

In this example, a rotational solenoid is used in order to rotate the rotating unit. The rotating unit may be controlled as outlined above with regard to FIG. 5*b*.

Once a droplet has been determined to exit the decoupler at a specific output, the droplet may be dispensed from the decoupler or the microfluidic device or chip. In this example, an xy-stage is provided in order to dispense a droplet at a desired location in the xy-plane, for example into a microtitre plate or other format. Furthermore, a pneumatic flow restrictor may be provided in order to more precisely control a flow rate for dispensing a droplet from the device. A thermocouple is, in this example, connected to a channel between an output of the decoupler and the pneumatic flow restrictor. One or more nozzles may be provided at the outputs of the decoupler. In this example, an additional fast solenoid valve is provided for controlling the dispensing of droplets.

In the example device of FIG. 6, a high pressure unit is provided which allows for dispensing droplets from the device via pressurised fluid ejection. The high pressure unit comprises, in this example, a compressed gas container, various pressure regulators for regulating the pressure in the channel network, and a T-junction which connects the compressed gas container and regulators with the pressure sensor. It will be appreciated that alternative configurations may allow for controlling the pressure in the channel network in order to eject a droplet via pressurised fluid ejection.

In this example, a waste container is connected to an outlet of the droplet sorting device. Droplets containing entities which are not of interest, or containing no entities, may be put to waste.

It will be appreciated that any of the inlets of the decoupler shown in FIG. 6 may be used as an outlet, and vice versa.

FIG. 7 shows schematic illustrations of a decoupler according to embodiments described herein.

Figure 7A:
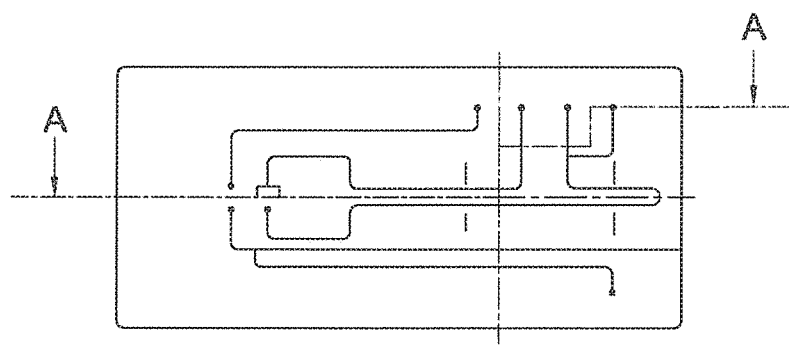
FIGS. 7a-7c show schematic illustrations of a decoupler according to embodiments of the present invention.

FIG. 7*a* shows a schematic top-view of an example decoupler. As can be seen, various inlets are provided on the decoupler. The inlets are connected via channels to a rotating unit of the decoupler. The rotating unit is further connected via a channel network to outlets of the decoupler at which a droplet may be dispensed from the device.

Figure 7B:
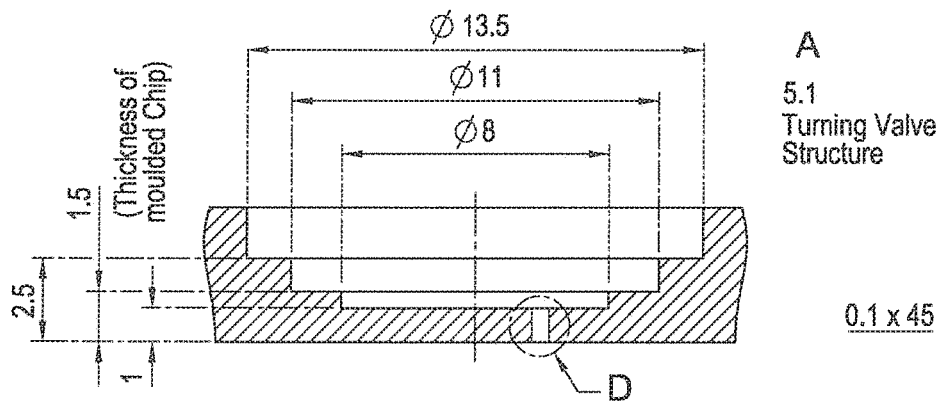

FIG. 7*b* shows a schematic side-view of the rotating unit of the decoupler. It will be appreciated that the dimensions of the rotating unit are merely exemplary. The rotating unit may comprise openings (D in FIG. 7*b*) at which a droplet may enter and/or exit the rotating unit.

Figure 7C:
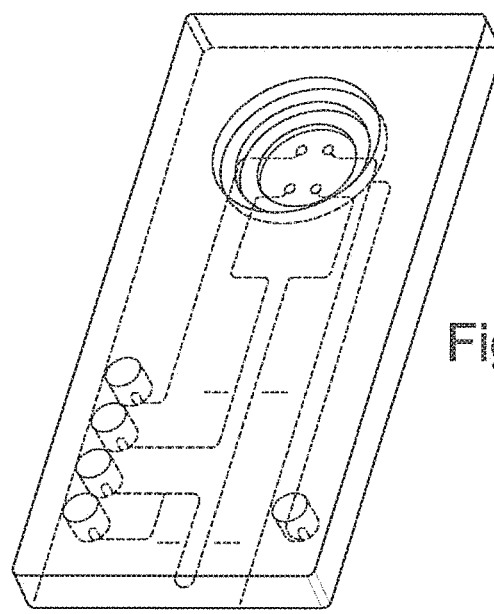

FIG. 7*c* shows a schematic perspective view of the decoupler with a rotating unit. In this example, four inlets and one outlet are provided. However, as outlined above, each of the inlets may also be used as an outlet, and the outlet may equally be used as an inlet, depending on the specific requirements of the device.

Figure 8:
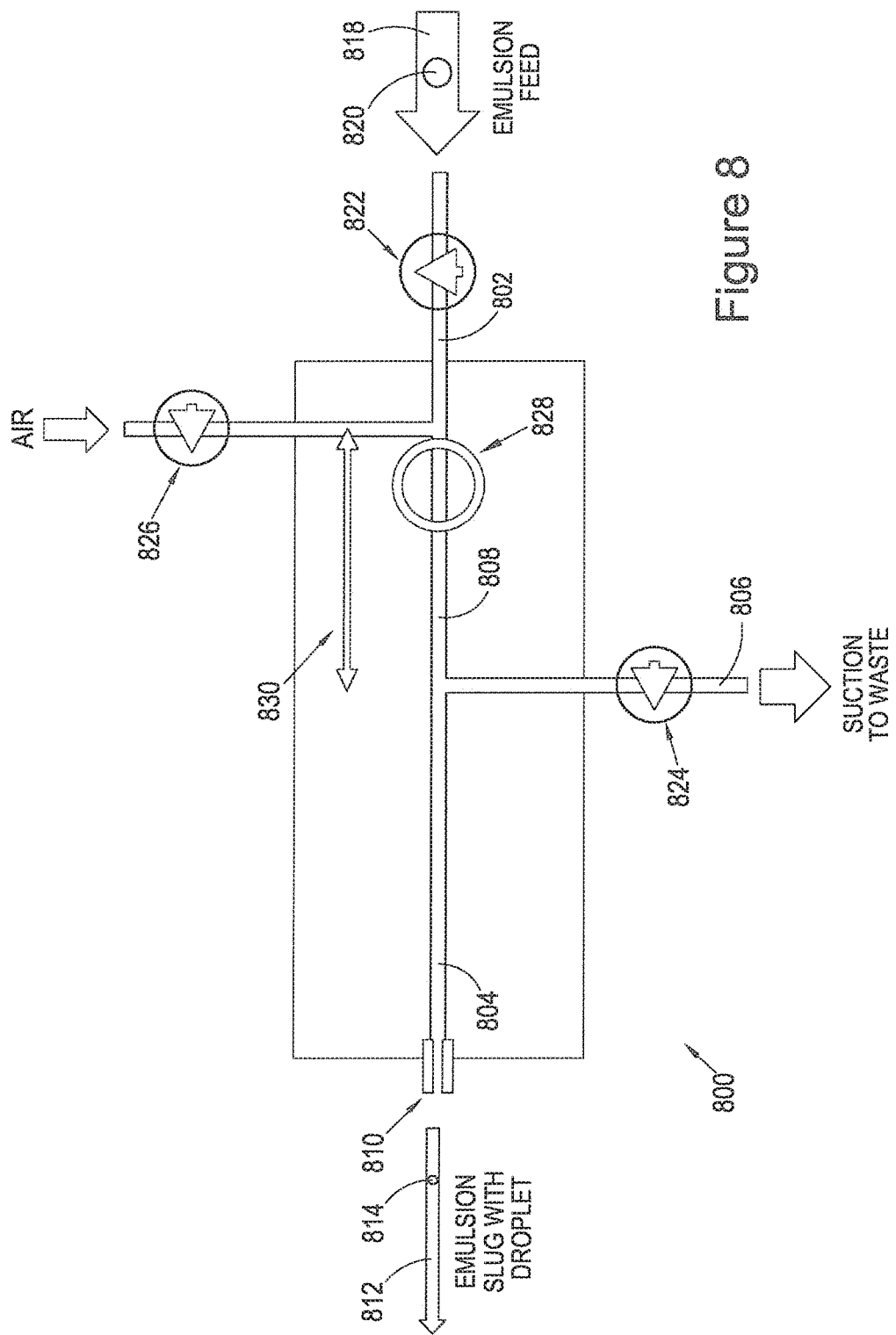
FIG. 8 shows a schematic illustration of a dispenser according to embodiments of the present invention.

Referring now to FIG. 8, this shows an example embodiment of a droplet dispenser 800. This comprises an input channel 802 and first and second output channels 804, 806 with a shared channel (flow) portion 808. Channel 804 is provided with a nozzle 810 at the outlet for dispensing a slug of emulsion 802 comprising a droplet 814. Channel 806 goes to waste, in embodiments under suction. The dispenser also has an air inlet 816 for a pressurised air supply. Input channel 802 receives an oil feed 818 with droplets 820 at intervals. The input channel 802 is provided with a feed valve 822; the waste output channel 806 is provided with a shut-off valve 824, and the air supply inlet 816 is priced with an air valve 826. In the illustrated example region 828 defines an optical droplet detection region. The separation 830 between the air inlet 816 and channel 806, which defines the length of the shared flow path between the two output channels 804, 806, defines the length of the ejected slug of emulsion 812.

When oil without a droplet, or oil with an unwanted droplet, is passing through the dispenser feed valve 822 is open and shut-off valve 824 is open so that the inlet fluid flow passes along the shared channel region 808 and is sucked down channel 806 to waste. When a droplet for dispensing is detected in channel 808, valves 822 and 824 are shut off and air valve 826 is opened to eject the slug of emulsion 812 containing the droplet 814 from channel 808 along output channel 804 and out via nozzle insert 810. A corresponding procedure may be implemented when a droplet for dispensing is predicted to be present in channel 808, in a system where droplet detection is performed upstream.

In embodiments the nozzle may be shaped so as to disrupt the slug of emulsion, more particularly the droplet and/or may be provided with a mesh for a similar purpose, so that when the slug/droplet is dispensed into a well containing an aqueous medium the droplet contents are liberated into the aqueous medium of the well rather than floating on top. Optionally the nozzle 810 may be equipped with other means for a similar purpose, for example on or more electrodes to generate an electric field; and/or an additional channel to carry a de-emulsification agent.

A rate control unit may optionally be provided in order to control the rate of droplets flowing into the droplet dispenser 800. The rate control unit may be coupled to a holding chamber in front of the droplet dispenser 800, which allows for feeding droplets to the droplet dispenser at a defined rate.

In some embodiments, channel 806 is wider compared to channel 804, such that a bias for droplets towards the waste channel 806 is generated. This may be particularly useful in embodiments, in which the microfluidic system or chip in which the droplet dispenser 800 is incorporated is employed in a vertical orientation, in which the aqueous droplets tend to flow towards the top of the system or chip. In embodiments in which the system or microfluidic chip is employed vertically, the channel 806 is therefore preferably arranged on the top side of the droplet dispenser 800.

Figure 9:
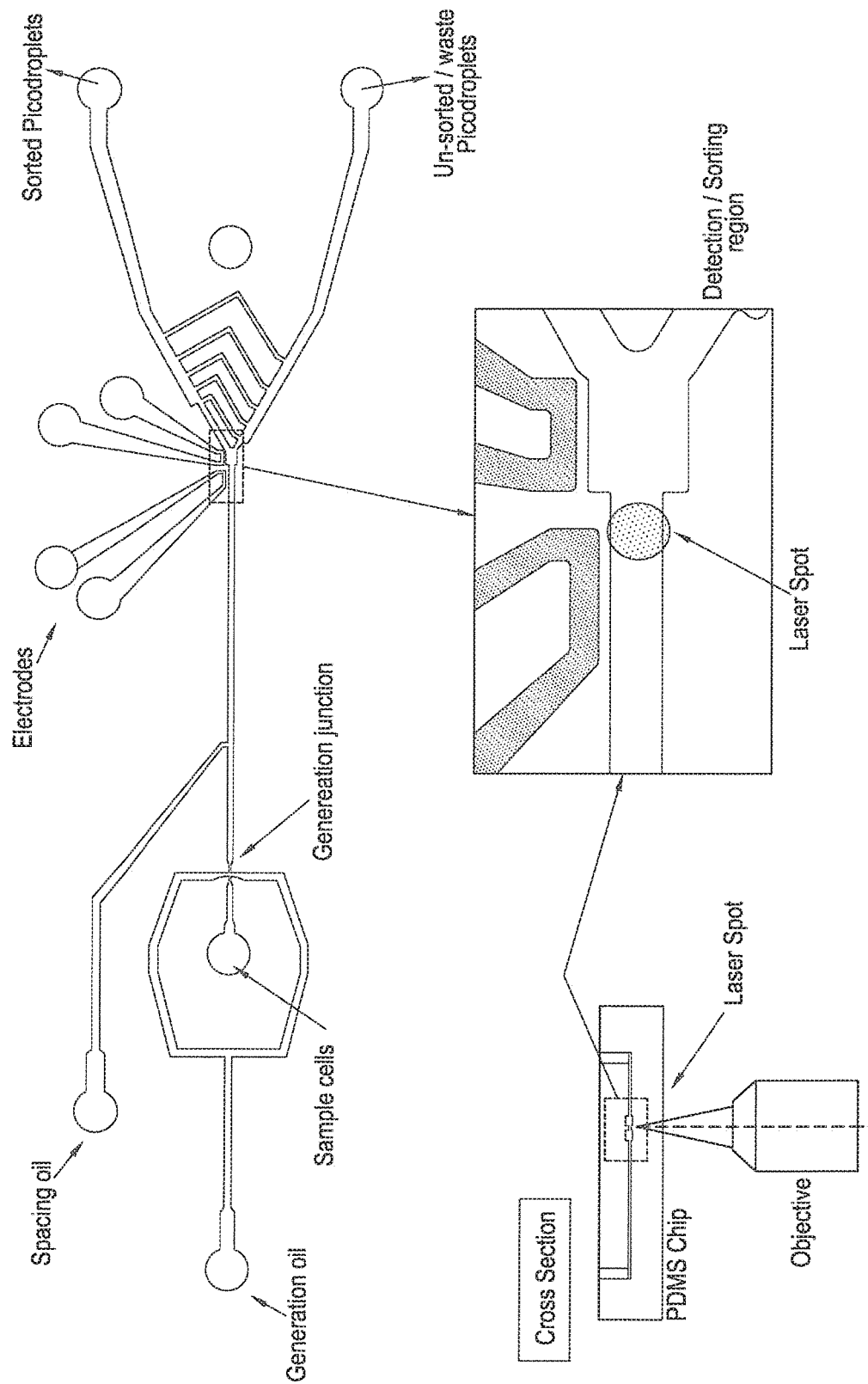
FIG. 9 shows an example droplet generation and sorting system for use in embodiments of the present invention.

FIG. 9 shows an example droplet generation and sorting system for use in embodiments of the present invention. Thus FIG. 9 shows an example of a system which may be implemented on a cartridge to implement the previously described droplet generation and sorting functions. Once the constituents (if any) of a droplet have been analysed, for example as outlined with regard to FIGS. 14*a* and 14*b*, the droplet may be sorted based on this analysis, in this example by applying an electric field using electrodes (shown in black in the inset Figure). The droplet sorting is, in this example, based on the dipole moment of a droplet, whereby a droplet experiences a different electric force depending on its constituents.

FIG. 10*a* shows a perspective view of a droplet processing cartridge 1000 according to an embodiment of the invention in which the sample/oil reservoirs are built into the cartridge. As illustrated the cartridge includes a region 1002 for actuating a valve of the cartridge, electrical connections 1004 for the sorting region, and a dispensing nozzle 1006 (hidden in the perspective view shown).

Figure 10B:
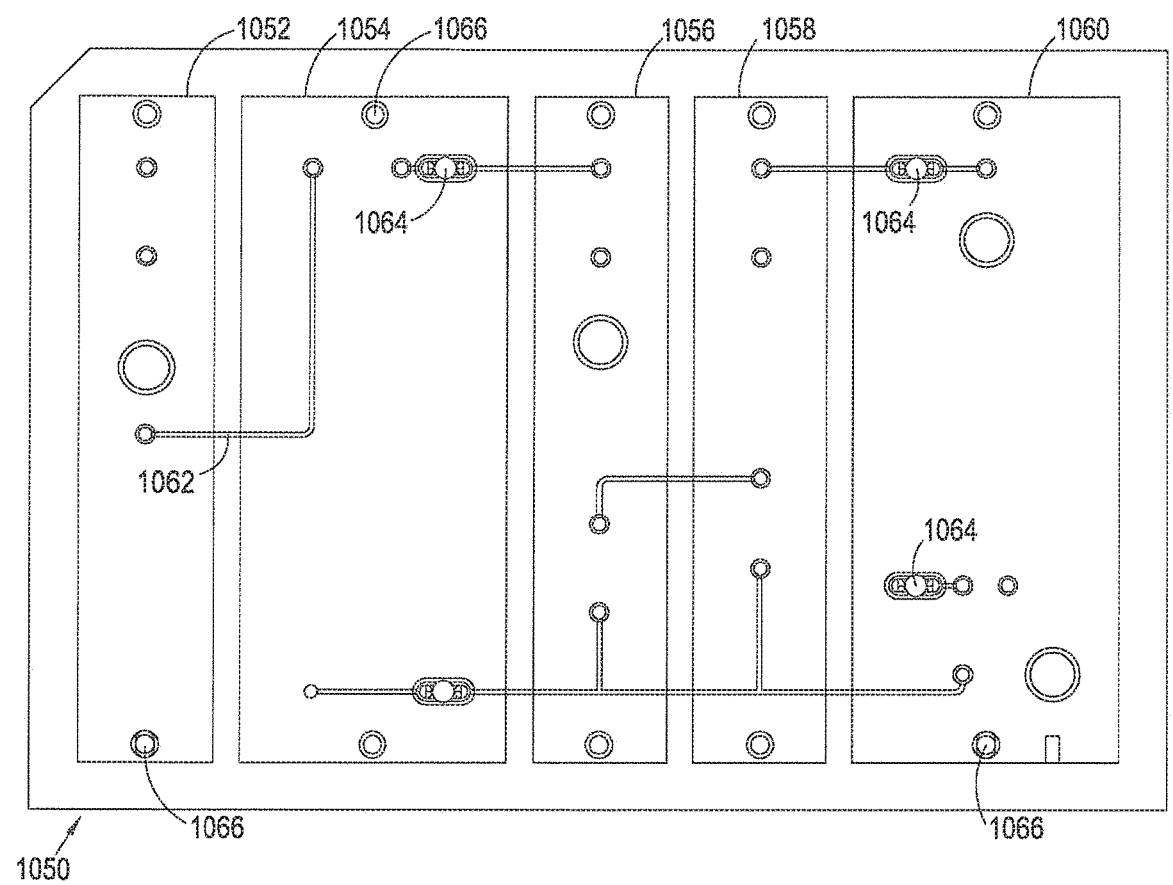

FIG. 10*b* shows a view from above of a modular cartridge 1050 according to an embodiment of the invention. The illustrated modular implementation comprises a droplet generation module 1052, a droplet incubation/storage module 1054, a droplet sorting module 1056, a droplet/hold (flow buffer) region 1058, and droplet dispensing region 1060. The illustration also shows on-cartridge connections 1062 ('manifold channels') between the modules, as well as locations of example valves 1064 and datum location bins 1066. In embodiments the channels 1062 are defined in a base plate of the cartridge over which is provided a gasket and then the modular droplet processing regions 1052-1060 are implemented by attaching separate plates over the gasket, preferably located by datum pins 1066.

Referring now to FIG. 11, this shows aspects of a control system for a microdroplet processing instrument according to an embodiment of the invention. The control system may be implemented on a general purpose or dedicated computer provided with various sensors and actuators, as described further below.

Figure 11A:
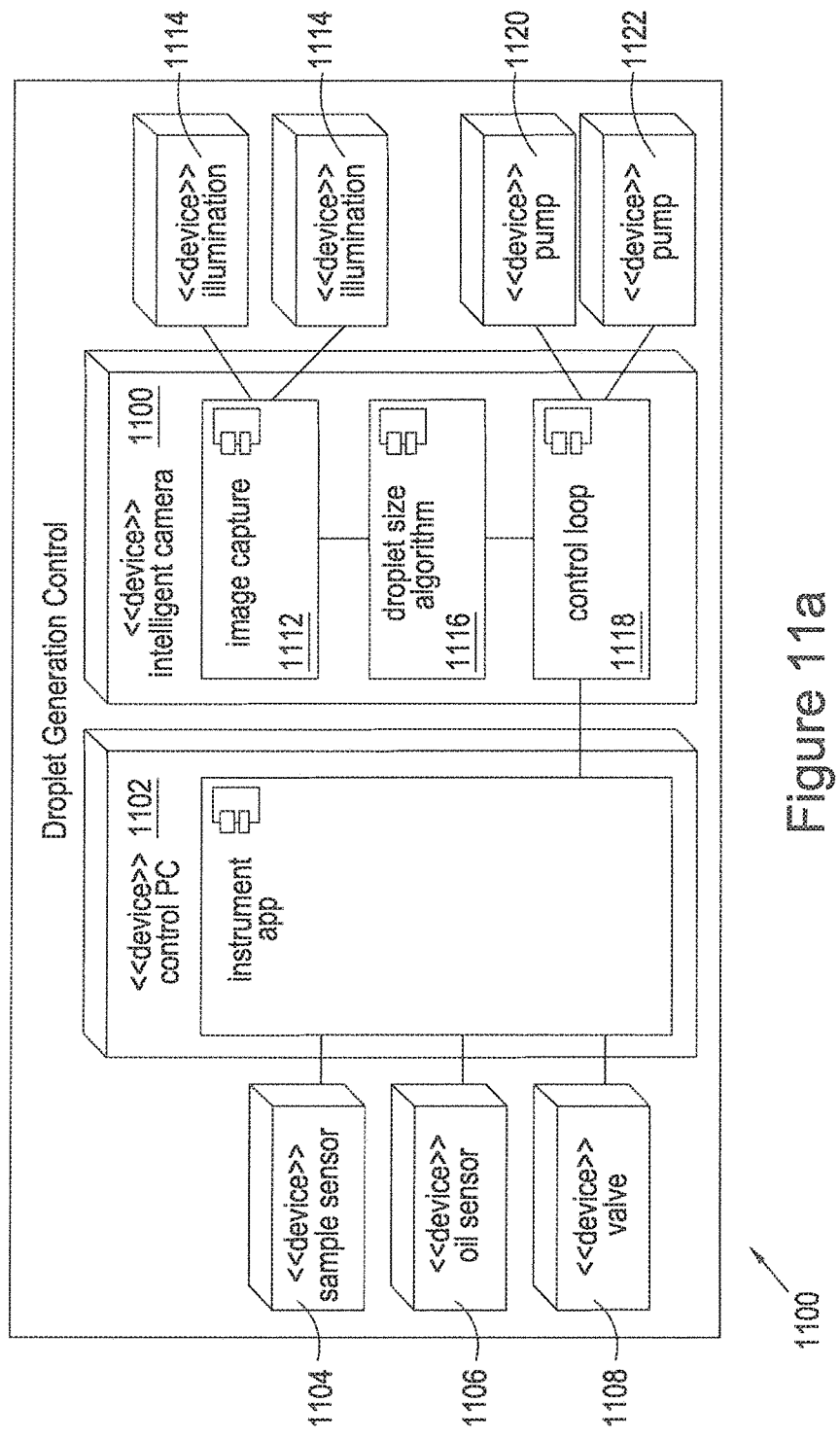
FIGS. 11a to 11d show an example control system for controlling a droplet processing system according to an embodiment of the invention.

Thus referring to FIG. 11*a*, this shows a droplet generation control systems 1100 comprising a control computer system 1102 coupled to sensors for the sample 1104 and oil 1106, and to control a valve 1108 for controlling emulsion generation. Controller 1102 is also coupled to an intelligent camera 1110, that is a camera with on-board processing. It will be appreciated however that, alternatively, the processing shown in the camera may be implemented by controller 1102 and that, vice-versa, in principle the functions of controller 1102 may be implemented on camera 1110. The intelligent camera comprises an image capture system 1112 which controls illumination 1114, for example light emitting diode (LED) illumination. The image capture module 1112 also includes a camera (not shown) to capture an image. The captured image is processed by a droplet size control procedure 1116, which implements a control loop 1118 to control pumps 1120, 1122 for controlling the rate of flow of the sample and oil to control the emulsion formation.

Figure 11B:
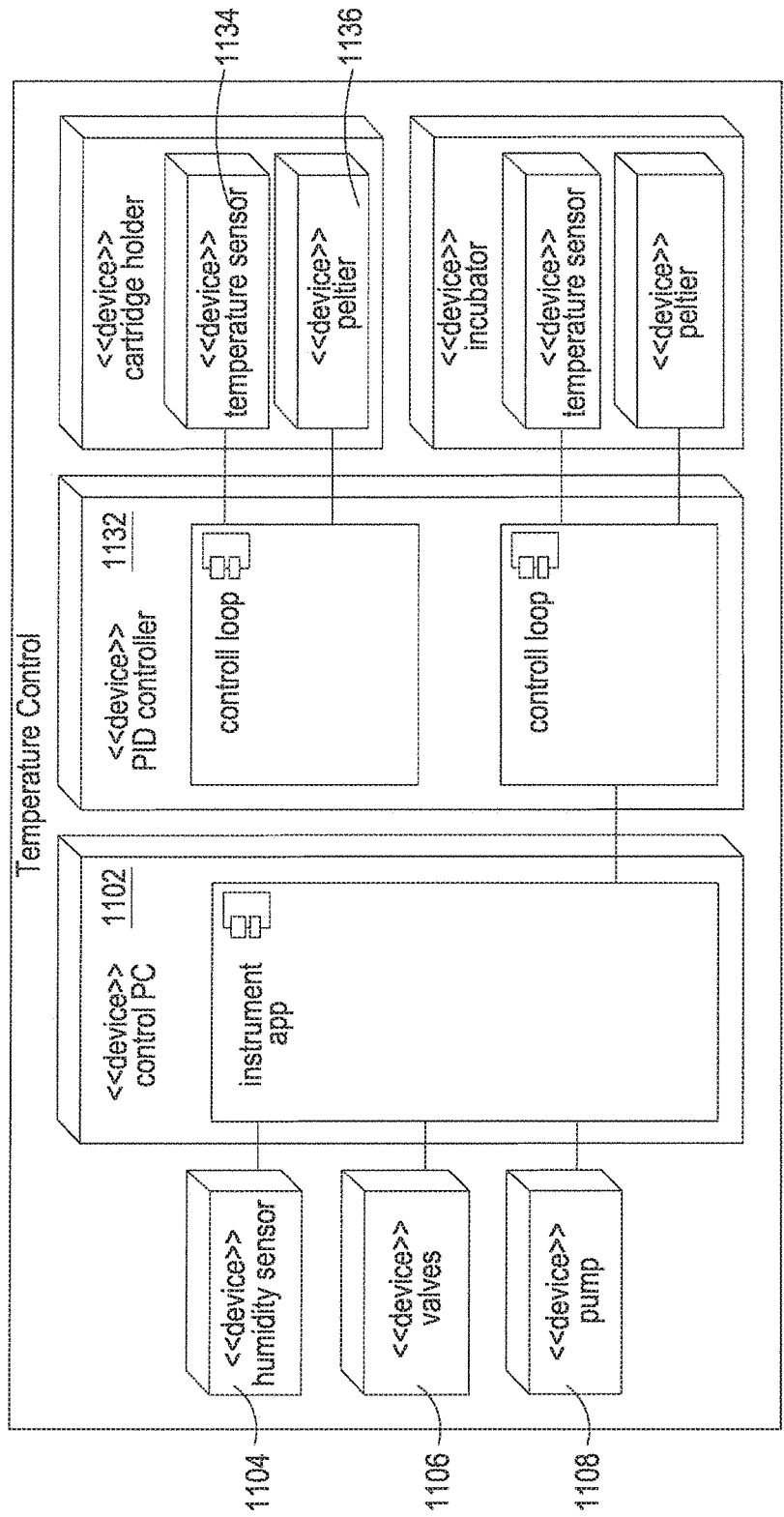

FIG. 11*b* shows a temperature control system 1130, in this example using the same controller 1102, in this example coupled to a PID (proportion-integral-derivative), controller 1132. This may implement one or more control loops each comprising a temperature sensor 1134 and a temperature control device, for example a heater (not shown) and/or a cooling device such as a Peltier effect device 1136. Optionally other sensors/control may also be implemented.

In some embodiments, a heating/cooling unit may be provided which allows for heating and cooling the entire system or the microfluidic chip. Heating and cooling may be performed locally in certain areas, e.g. in specific areas of the microfluidic chip only. For example, heating and cooling may be provided at the incubator of the system or microfluidic chip. In some embodiments, the temperature of the system or microfluidic chip is set to 8-10 deg C. The heating/cooling unit may then be used to increase the temperature to 37 deg C., for example in the incubator, and the temperature may subsequently be reduced back to 8-10 deg C., in order to, e.g. stop any biological activity in the cells or other entities stored in the droplets. Embodiments described herein may therefore allow for polymerase chain reaction (PCR) of biological entities, which generally consists of cycles of repeated heating and cooling. The droplets may then be sorted subsequent to the heating/cooling cycle(s).

Figure 11C:
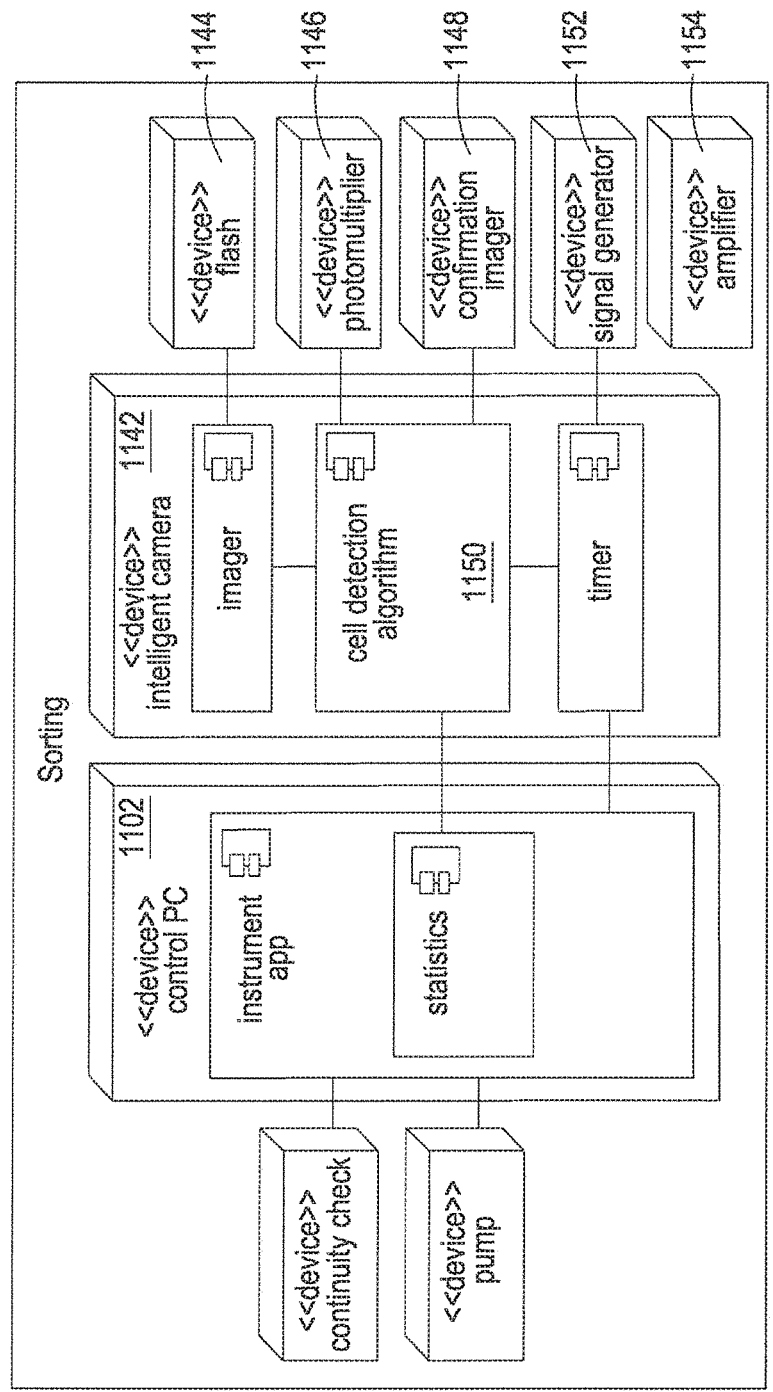

FIG. 11*c* illustrates a droplet sorting control system 1140, also comprising an intelligent camera 1142 (although again a dumb camera may alternatively be employed). In the illustrated example the sorting system comprises a droplet flash illumination device 1144, a photomultiplier 1146 for cell detection, and an optional further imaging device 1148 for cell detection confirmation, preferably all operating under the control of a cell detection algorithm 1150. The sorting control system also includes a signal generator 1152 and optional amplifier 1154, to provide a control signal to the sorting electrodes described previously.

Figure 11D:
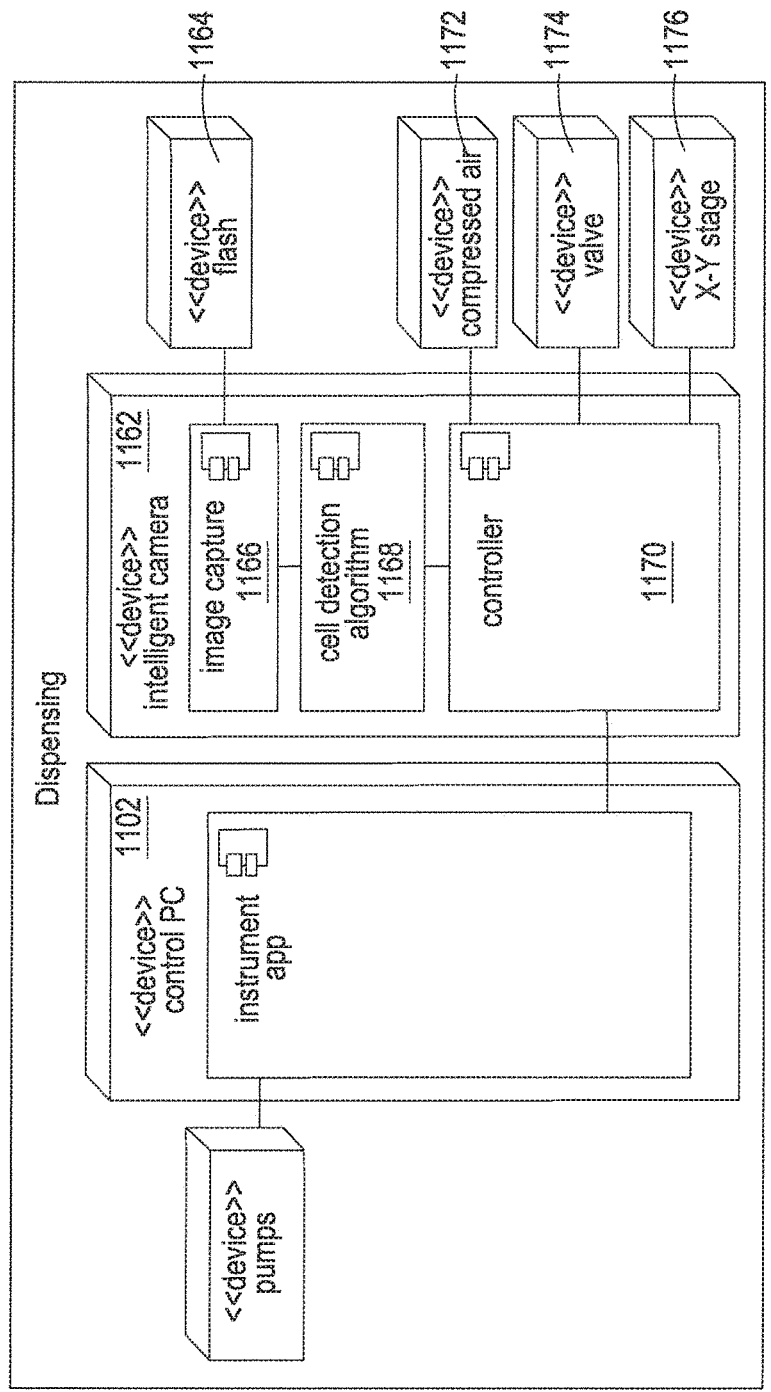

FIG. 11*d* shows a droplet dispensing control system 1160, in the illustrated example comprising a further intelligent camera 1162, (although again this may be a dumb camera), with processing performed by controller 1102. In the illustrated example camera 1162 controls droplet illumination, in particular flash device 1164, and implements an image capture procedure 1166 from imaging device (not shown) to detect droplet contents, for example a cell, using a cell detection algorithm 1168. A control procedure 1170 controls a source of compressed air 1172, optionally a valve 1174 (such as valve 477 of FIG. 4*a*) and an X-Y stage 1176 holding the multi-well plate 484.

Figure 12:
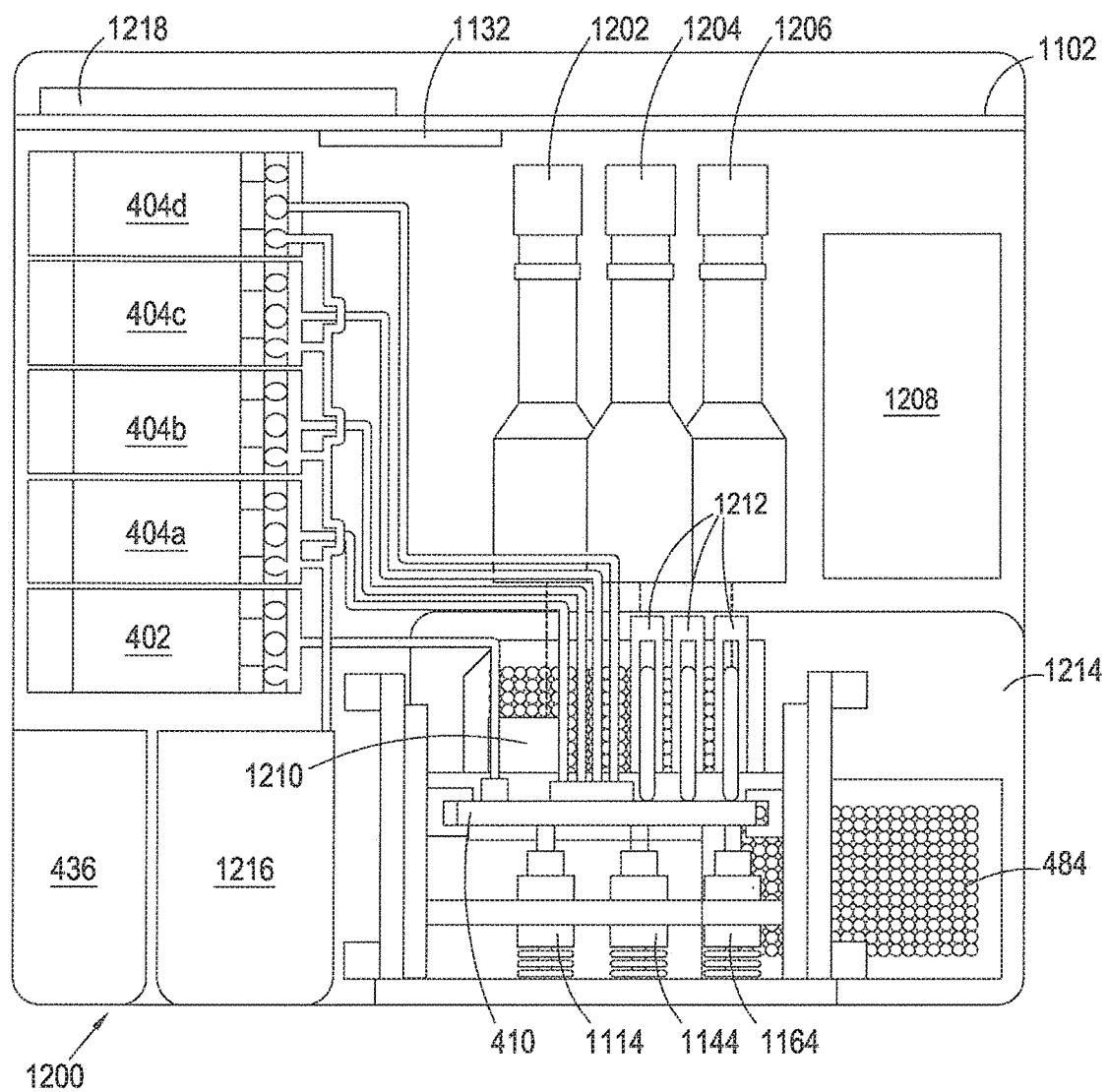
FIG. 12 shows an example physical configuration of a droplet processing system according to an embodiment of the invention

FIG. 12 shows an example physical configuration of a droplet processing instrument 1200, in which like elements to those previously described are indicated by like reference numerals. FIG. 12 shows locations of intelligent cameras 1202, 1204, 1206 for, respectively, droplet generation, sorting and dispensing. These have respective (LED) illumination 1114, 1144, 1164 under control of an LED controller 1208. The system also illustrates the cartridge 410 and a heater plate 1210 of an incubator for the cartridge, and valve actuators 1212 for droplet generation and incubation. The multi-well plate 484 is mounted on an X-Y stage 1214. FIG. 12 further shows the sample reservoir 402 and oil reservoirs and pumps 404*a*-*d* to provide oil for droplet generation, sorting, spacing and dispensing. The instrument also includes an internal oil container 1216 to supply these reservoirs, and a waste oil container 436. The instrument includes the previously described control system, as well as a user interface 1218.

Figure 13:
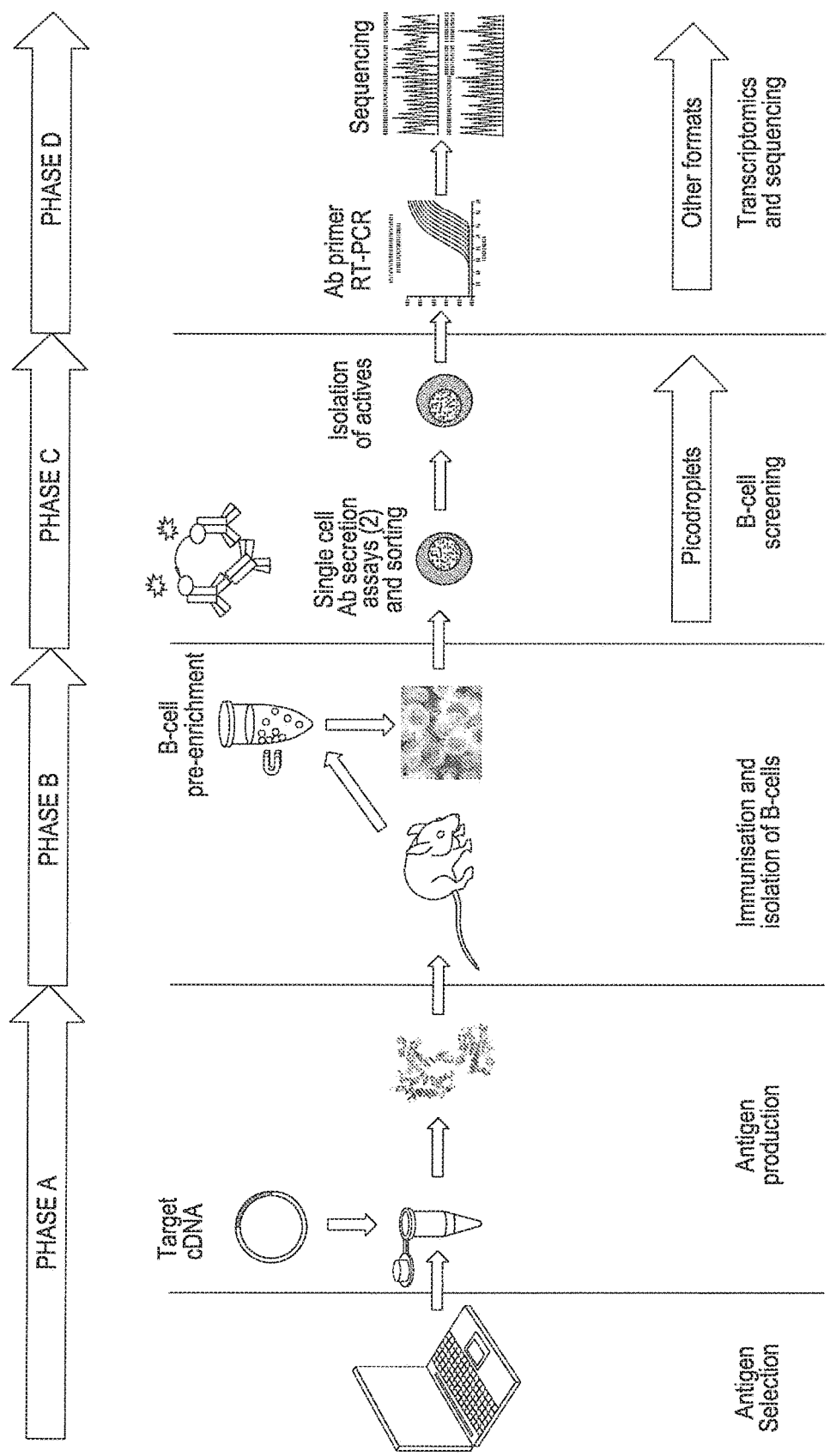
FIG. 13 shows a schematic diagram of phases for cell analysis.

FIG. 13 shows a schematic diagram of phases for cell analysis: Devices and methods known to those skilled in the art are implemented in phases A, B and D. Antigens are selected and produced in phase A according to standard techniques. Immunization and isolation of, in this example, B-cells may be performed in phase B in order to obtain a fluid containing cells to be sorted and/or analysed according to embodiments described herein. At phase C, single cells may be obtained in a single droplet using embodiments of the devices and methods described herein. A viable cell in a single picodroplet may be provided, based on which further experiments may be conducted in phase D, in this example transcriptomics and sequencing experiments.

Figure 14B:
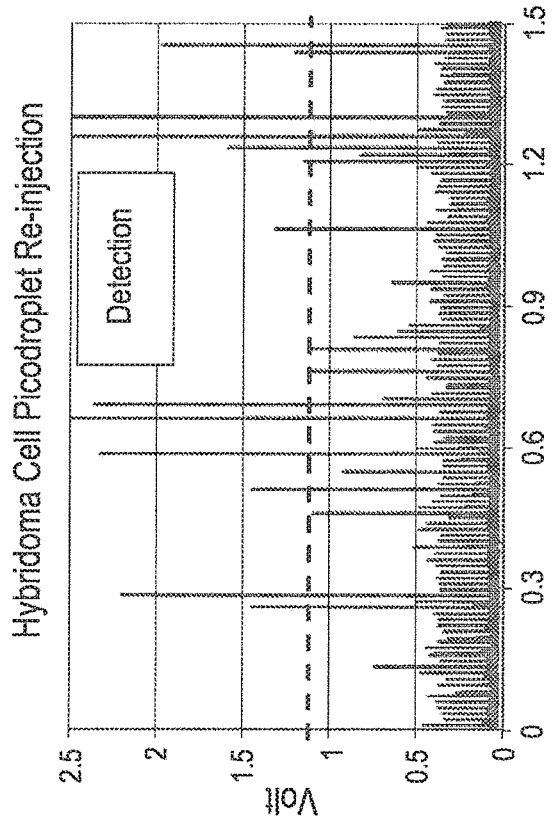
FIGS. 14a and 14b show a schematic illustration of a method of determining contents of a droplet.
Figure 14A:
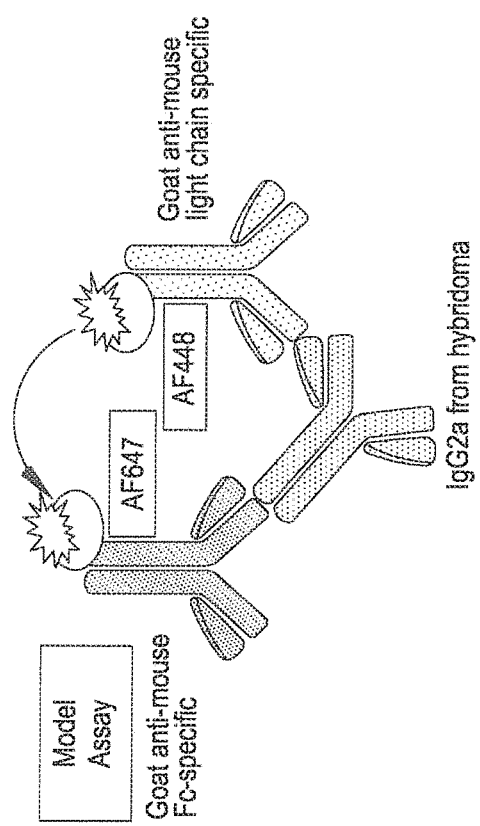

FIGS. 14a and 14b show a schematic illustration of a method of determining contents of a droplet. In this example, two fluorescent dyes, AF647 and AF488, are provided in a picodroplet. When, in this example, a hybridoma cell is present in the picodroplet, a product of the hybridoma, such as a protein or antibody may bind to each of the AF647 and AF488 fluorescent dyes (each of which has an associated antibody to bind to a different respective portion of the hybridoma product). The binding thereby allows for Fluorescence Resonance Energy Transfer (FRET) to take place between the AF647 and AF488 fluorescent dyes, resulting in a change in fluorescence. Thus a signal, in this example an optical signal, is produced if an interaction occurs allowing selective detection of a product of the biological entity, in this example, cell.

FIG. 14b shows fluorescence detection based on the presence of, in this example, one or more hybridoma cells in a picodroplet. Once a signal above a threshold is detected, a hybridoma cell has been identified in the picodroplet. The background of, in this example, approximately 0.5V is due to empty picodroplets which are provided to the analyser. Therefore, a droplet resulting in a signal above a threshold, in this example of approximately 1.1V, may be collected for further sorting, and/or analysis, and/or growth. Droplets which give rise to a signal below this threshold may be put to waste, as desired.

It will be appreciated that the donor and acceptor fluors may be optimized for a range of FRET assays, and depending on one or more specific cells or other entities to be detected in a droplet.

The fluorescence detection shown in FIGS. 14a and 14b may be used, for example, in the droplet sorting device and/or in the decoupler as outlined above.

Figure 15:
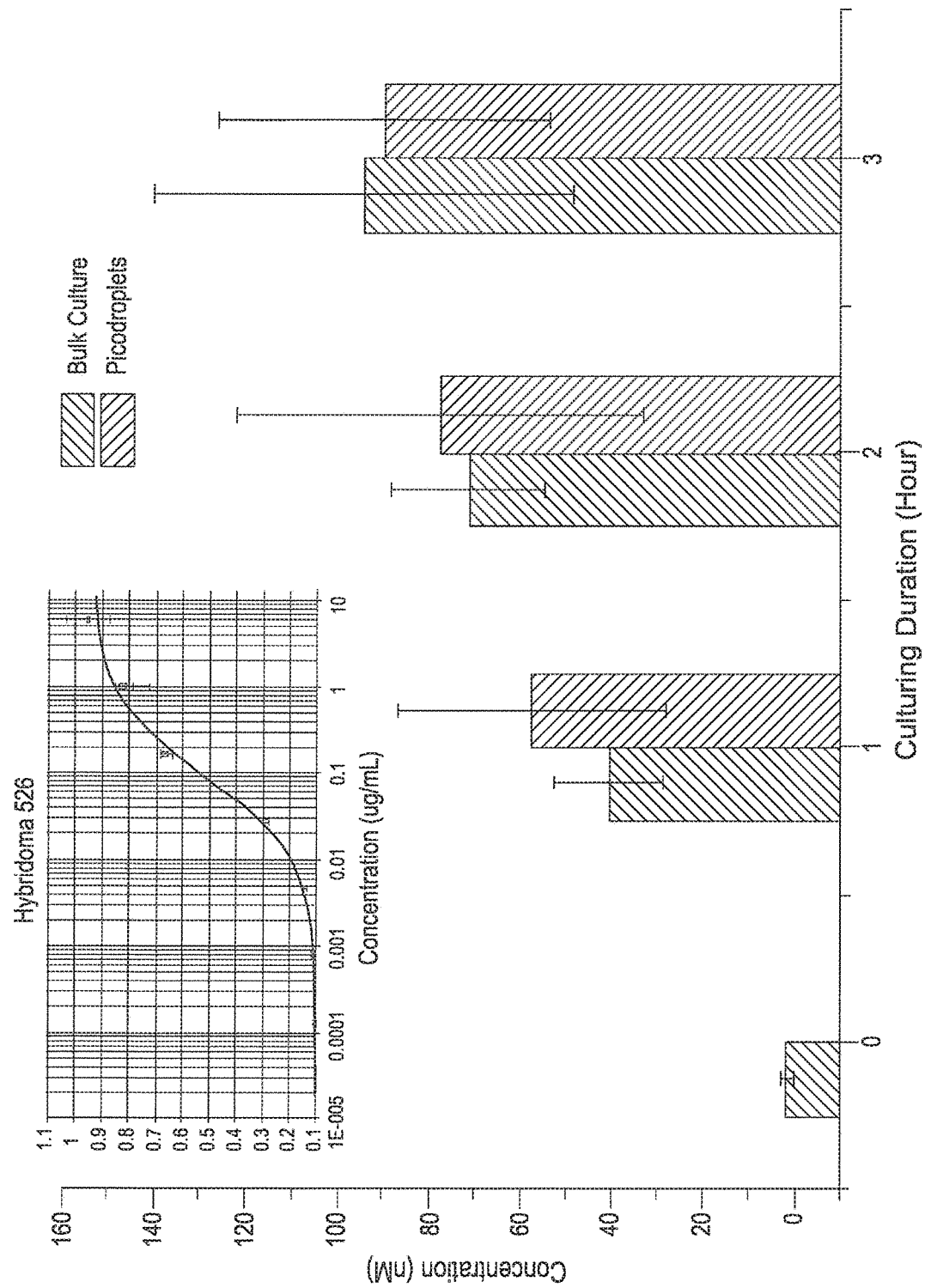
FIG. 15 shows monoclonal antibodies secretion in picodroplets by hybridomas.

FIG. 15 shows monoclonal antibodies secretion in picodroplets by hybridomas. The measurements were performed using a FRET-based ELISA.

The graph shows the concentration of antibodies produced versus culturing duration. The dark bars represent a bulk culture which is grown from a standard test tube incorporating multiple cells. The red bars represent a sample in which a single cell is provided in a picodroplet (the volume of which was approximately 700 pl). The inset in FIG. 15 shows fluorescence intensity versus concentration.

As can be seen, the number of antibodies produced is comparable between the culture grown from a bulk culture and that grown from a single cell after a period of 1 hour or longer—it will be appreciated that the concentration at t=0 of a single cell in a picodroplet is negligible. As outlined above, it may be advantageous though to grow a cell culture from a single cell as this ensures a high monoclonality across the cell population. This shows that the concentration of cells grown from a cell in a picodroplet prepared according to embodiments described herein may be as high as or even higher than that grown from multiple cells in a standard test tube, whereby a higher monoclonality assurance is achieved for the population grown from a single entity.

Figure 16A:
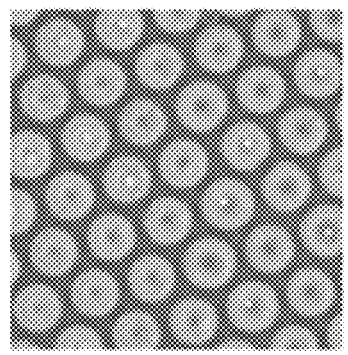
FIGS. 16a to 16d show populations of Chinese hamster ovary cells.
Figure 16B:
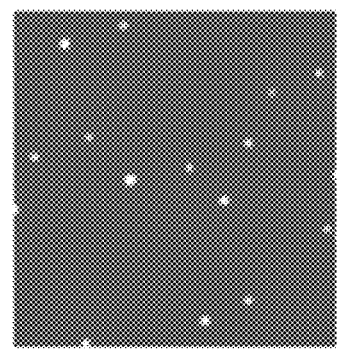
Figure 16C:
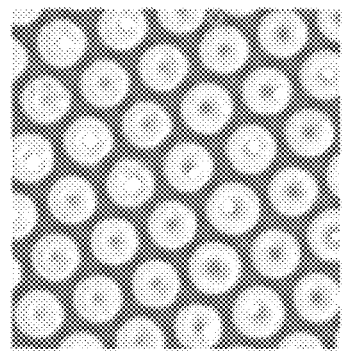

FIGS. 16a to 16c show optical images of populations of Chinese hamster ovary (CHO-S) cells. In this example, the picodroplets have an average diameter of approximately 84 μm and an average volume of approximately 300 pl. In FIG. 16a, the cells can be seen under a bright field. In order to determine whether a cell is viable or not, a fluorescent dye, in this example DRAQ-7, may be provided (FIG. 16b). The merged image is shown in FIG. 16c; viable cells show a green fluorescence in FIG. 16c.

Figure 16D:
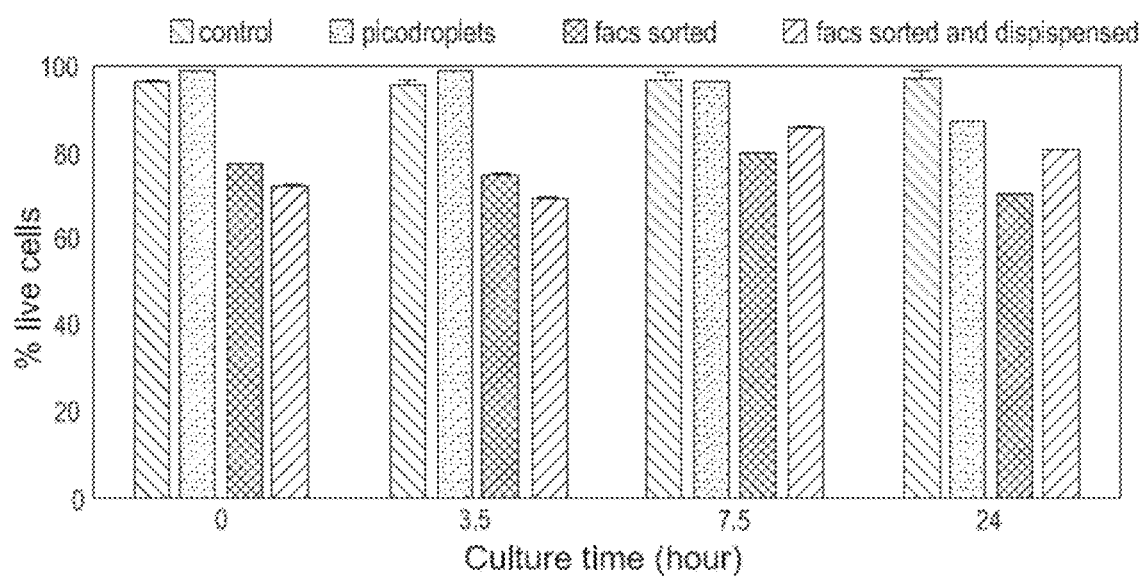

The percentage of viable (i.e. living) CHO-S cells versus culture time is shown in FIG. 16d for various techniques. The blue bars show control cultures. The green bars represent cell cultures obtained via the picodroplets preparation techniques according to embodiments described herein. The purple bars show the analysis for populations grown from droplet sorted by FACS, and the pink bars represent populations sorted and dispensed using FACS.

As can be seen, the percentage of viable cells grown from samples prepared using embodiments described herein are significantly higher than those obtained via FACS techniques. This result shows that encapsulation of a cell (or cells) in a picodroplet has no measureable effect on cell viability, demonstrating the advantages of the droplet preparation, sorting and dispensing according to the above described embodiments.

Figure 17:
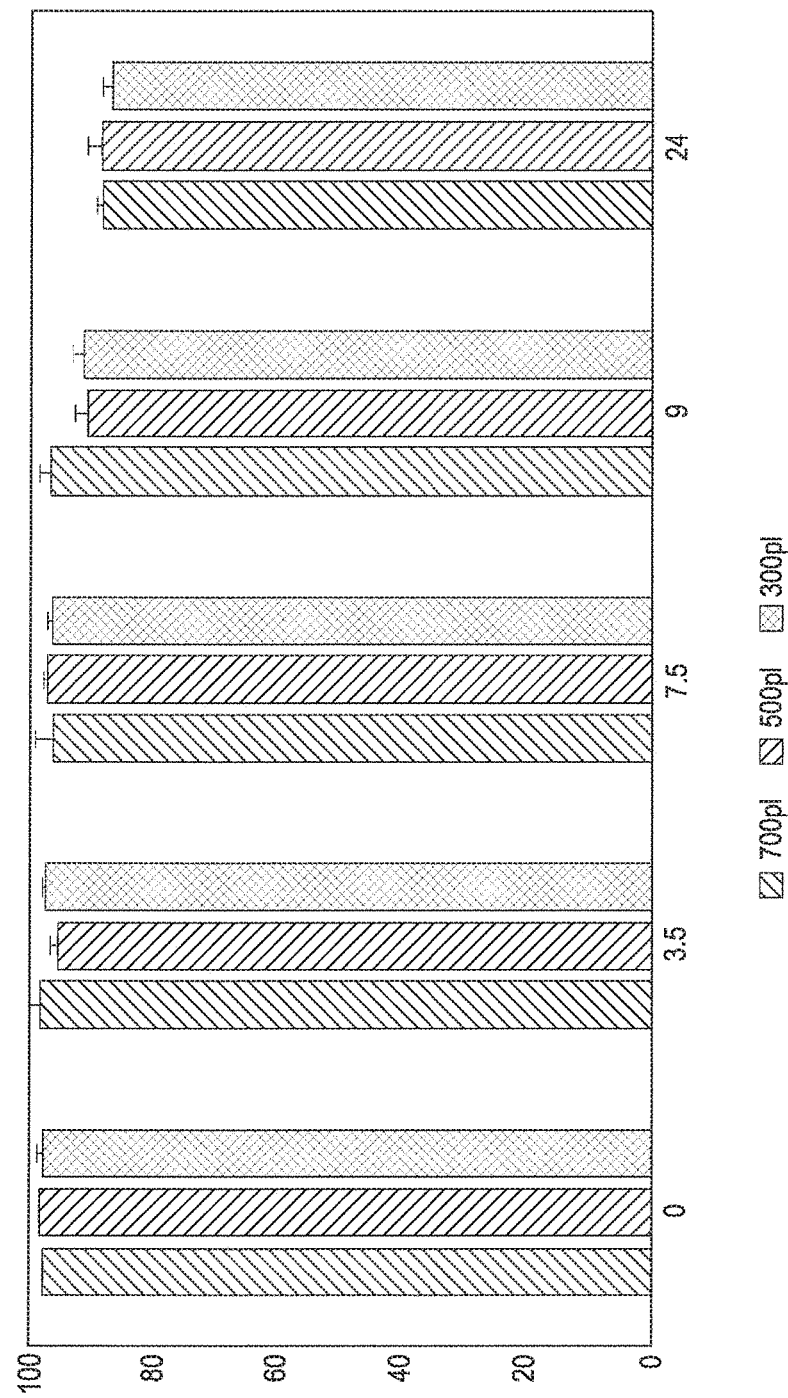
FIG. 17 shows percentage of viable CHO-S cells versus culture time for different picodroplet sizes.

FIG. 17 shows percentage of viable CHO-S cells versus culture time for different picodroplet sizes, in this example 300 pl, 500 pl and 700 pl. This analysis may allow determining whether the size of a picodroplet may be decreased in order to increase generation rates.

It can be seen that generally the percentage of viable cells is similar for all picodroplet sizes which were investigated. However, after certain culture times, for example 9 hours, the picodroplet with a volume of 700 pl contained the highest percentage of viable cells. This may be expected as a larger volume of the droplet may provide nutrients to the cells for a longer period of time, such that the cells will survive for a longer period of time.

Figure 18A:
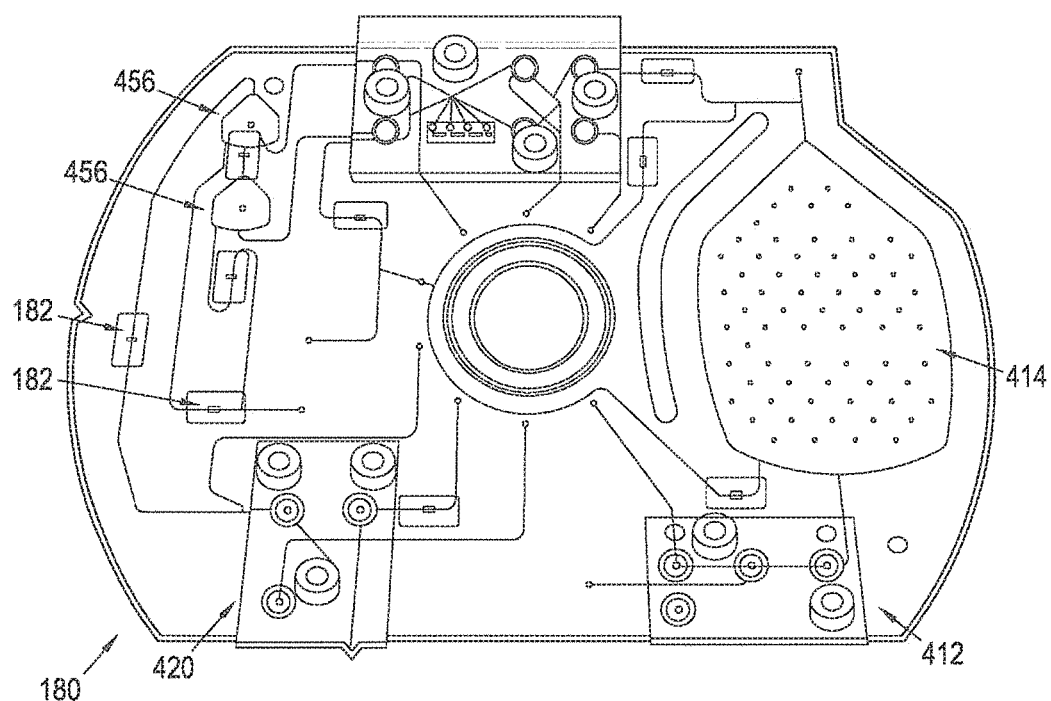
FIGS. 18a and b show a microfluidic chip and a schematic block-diagram of a control system, respectively, according to embodiments of the present invention.

FIG. 18a shows an image of a microfluidic chip 180 according to embodiments described herein.

The microfluidic chip 180 integrates various modules of the system as described throughout the specification into a single chip design. The microfluidic chip 180 comprises, in this example, a droplet generation region 412, a droplet incubator/storage region 414, a droplet sorting region 416 and a droplet dispensing region 420. In this example, the microfluidic chip 180 comprises storage chambers 456 and valves 182 which allow for delaying transport of the droplets throughout the microfluidic chip 180, if desired, as the droplets may be held in the chamber 456 for a controllable period of time (e.g. from seconds to minutes).

The holding chambers 456 of the microfluidic chip 180 are preferably as close as technically possible to the droplet dispensing region 420. This allows for a better control of droplet transport and dispensing, which may be particularly difficult as the aqueous droplets may have a different flow rate compared to oil. The closer the holding chambers 456 are to the droplet dispensing region 420 (or droplet dispensing unit), the more controllable the droplet dispensing is, as the time of a droplet being transported between the holding chambers 456 and the droplet dispensing region 420 can be decreased. This may be particularly important in chip designs which are operated vertically, whereby the droplets float to the top of the chip.

In embodiments of the microfluidic chip 180, a control sequence is used which allows for isolating different workflows of different parts and regions of the microfluidic chip 180. For example, a droplet may be provided from the droplet generation region 412 directly to the droplet sorting region 416 before it reaches the droplet dispensing region 420. In this example, the droplet incubation/storage region 414 between the droplet generation region 412 and the droplet sorting region 416 is omitted. It will be appreciated that different (one or more) parts/regions of the microfluidic chip 180 may be omitted.

Figure 18B:
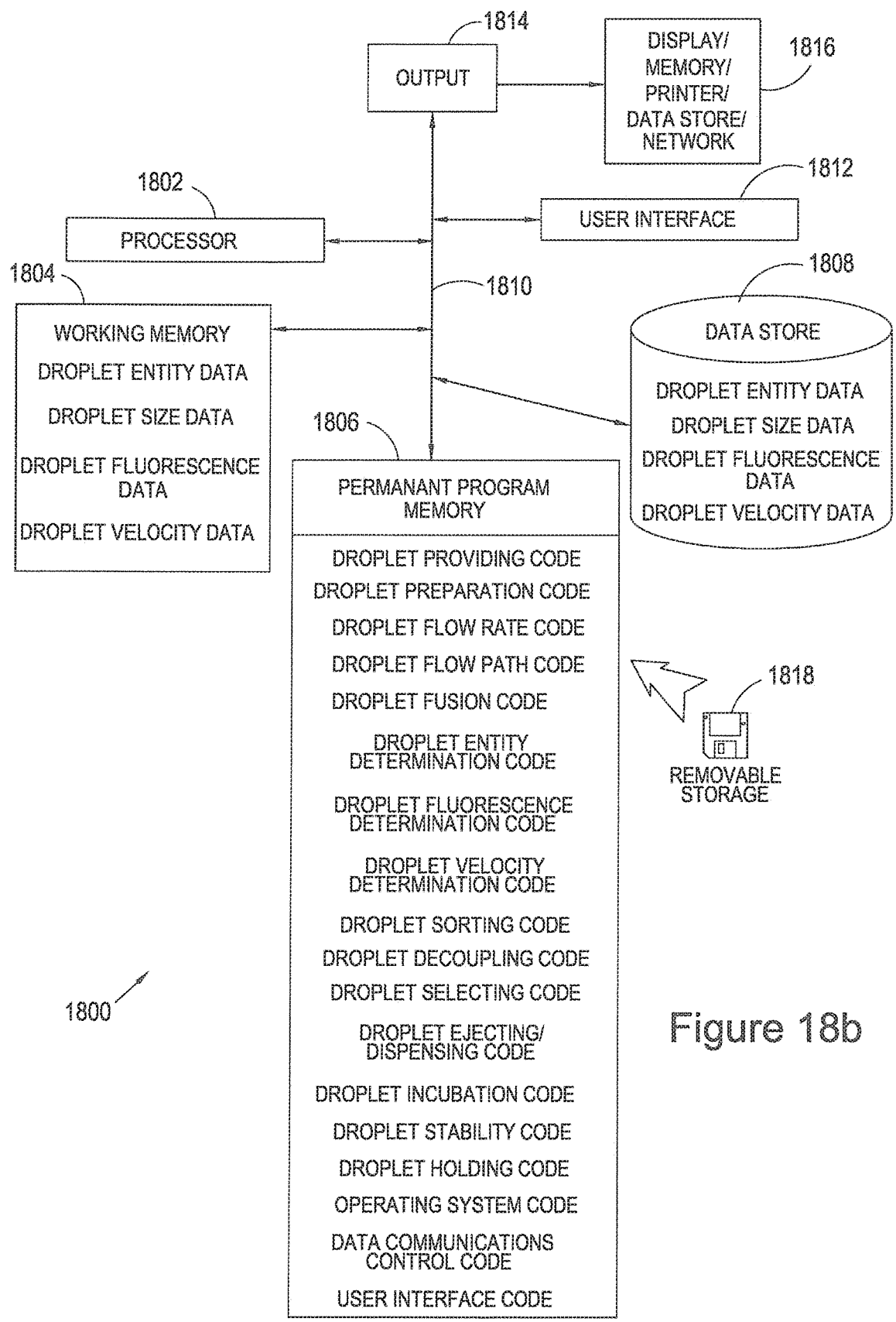

FIG. 18b shows a schematic block-diagram of a control system 1800 for operating the microfluidic chip shown in FIG. 18a. It will be appreciated that the control system 1800 may equally be used for operating the above-described microfluidic system, the droplet sorting or dispensing device, the droplet dispenser, the microfluidic device, the microfluidic cartridge, the microfluidic processing system and the instrument for microdroplet-based processing of biological entities. Therefore, the control system 1800 may be used in system in which one or more of the droplet generation device/unit, the droplet storage/incubation device/unit, the droplet sorting device/unit and the droplet dispensing unit/droplet dispenser are not incorporated into a single chip design.

Broadly speaking, the control system 1800 comprises a suitably programmed general purpose processor 1802. The control system 1800 further comprises working memory 1804, permanent program memory 1806 and a data store 1808, all linked by a common data and controller 1810. In this example, a user interface 1812 is also provided for configuring the system. The control system 1800 also includes an output 1814 connected to one or more of a display, a memory, a printer, a data store and a network 1816 to display, store, print or distribute for example data which correlates one or more properties of a droplet (or one or more properties of one or more entities in the droplet(s)) with its location in, e.g. a microtitre plate. The skilled person will appreciate that additionally or alternatively other forms of storage/output may be employed.

In this example, working memory 1804 is used for holding (which may be transient), processing and manipulating droplet entity data, droplet size data, droplet fluorescence data, droplet velocity data, and other physical and/or chemical data/properties regarding the droplet(s) and/or its entity/entities.

Permanent program memory 1806 stores, in this example, operating system code (which can be platform independent) comprising (optional) user interface code, operating system code, data communications control code for controlling the interfaces to the output, droplet providing code for controlling providing droplets from, e.g. a reservoir to the droplet processing system/microfluidic chip, droplet preparation code for controlling droplet preparation from, e.g. the solution comprising for example biological entities, droplet flow rate code for controlling a flow rate of the droplet(s) in the water-in-oil emulsion in the droplet processing system/microfluidic chip, droplet flow path code for controlling a flow path of droplets in one or more parts of the droplet processing system/microfluidic chip (e.g. one region or processing step, e.g. incubation, may be omitted and the droplet may be provided from one region/processing unit directly to another one), droplet fusion code for controlling fusion of droplets, droplet entity determination code for controlling the determination/identification of one or more entities in a droplet, droplet fluorescence detection code for controlling the detection of fluorescence o droplets and the processing thereof, droplet velocity determination code for controlling the determination of the velocity of droplets in the droplet processing system/microfluidic chip, droplet sorting code for controlling sorting of droplets in the droplet sorting unit/region, droplet decoupling code for controlling a decoupling of a droplet from a first fluidic flow path to a second fluidic flow path, droplet selecting code for controlling selecting of a droplet based on, e.g. previously obtained data of one or more properties of the droplet and/or its entities, droplet ejecting/dispensing code for controlling ejecting/dispensing of droplets by, e.g. regulating a pressure in the droplet processing system/microfluidic chip at one or more regions of one or more flow paths, droplet incubation code for controlling incubation of droplets, droplet stability test code for controlling a stability test performed on one or more droplets, and droplet holding code for controlling holding of droplets in holding chambers.

These codes are loaded and implemented by processor 1802 to provide corresponding functions for control system 1800.

Some or all of these codes may be provided on a carrier medium, illustratively shown by removable storage medium 1818, for example a CD-ROM.

Data store 1808 stores, in this example, droplet entity data which provides information about the one or more entities stored in a droplet (and whether a droplet does or does not contain any entities, e.g. biological entities), droplet size data which provides information of the size of the droplet(s), droplet fluorescence data which provides information about the fluorescence properties of the droplet(s), and droplet velocity data which provides information about the velocity of the droplet(s) at a certain location and/or region in the droplet processing system/microfluidic chip at a given time. The skilled person will appreciate that other physical and/or chemical properties of the droplet(s) and/or its entity or entities may be stored in data store 1808.

The invention further provides processor control code to implement the above-described systems and methods, for example on a general purpose computer system or on a digital signal processor (DSP). The code is provided on a non-transitory physical data carrier such as a disk, CD- or DVD-ROM, programmed memory such as non-volatile memory (e.g. Flash) or read-only memory (Firmware). Code (and/or data) to implement embodiments of the invention may comprise source, object or executable code in a conventional programming language (interpreted or compiled) such as C, or assembly code, or code for a hardware description language. As the skilled person will appreciate, such code and/or data may be distributed between a plurality of coupled components in communication with one another.

We now describe some example control sequences for use with embodiments of the chip. Control of the microfluidic chip (cartridge) can be achieved through software control of the instrument. In embodiments sequences of hardware control commands or scripts are sent to a hardware/software control interpreter and this information is converted into commands specific to hardware components.

Following loading of a sample onto the chip (e.g. a sample of cells or other biological or assay-related materials), the chip is loaded onto the instrument. A variety of operational modes are possible; these modes are implemented by selection of suitable command control sequences (control scripts). Two examples of modes of operation of the instrument are outlined below: (1) Monoclonality Assurance Mode; and (2) Direct Assay Mode.

An example of a chip control sequence for a Monoclonality Assurance Mode sequence is as follows:

Typical initialisation steps are sample loading and chip priming (where the channels and cavities of the chip are filled with oil so that there are no air bubbles). The steps then continue with:
  1. Picodroplet generation and sample encapsulation
  2. Optical detection of monoclonality (for example based on imaging and/or scatter)

3. Picodroplet sorting (based on optical signals)
4. Picodroplet collection
5. Picodroplet dispensing (preferably including optical detection/confirmation of monoclonality as previously described).

After a droplet has been dispensed in a slug of emulsion the slug enters a (microtitre plate) well, typically already containing water. There through physical action, and/or by other means, for example an electric field, the cell is released from the droplet into the water and collected in the well, the oil separating from the water. When the system operation is completed the system/chip is preferably cleaned.

An example of a chip control sequence for a Direct Assay Mode may have the same initialisation and payload collection steps as described above for the Monoclonality Assurance Mode. In addition the Direct Assay Mode may include the steps of:
1. Picodroplet generation and sample encapsulation
2. Incubation (for example at 37° C.)
3. Optical detection of monoclonality (for example based on imaging and/or scatter)
4. Optical detection for the assay (for example fluorescence and/or luminescence)
5. Picodroplet sorting (based on optical signals)
6. Picodroplet collection (assay positive)
7. Picodroplet dispensing (preferably including optical detection/confirmation of monoclonality as previously described).

Figure 19A:
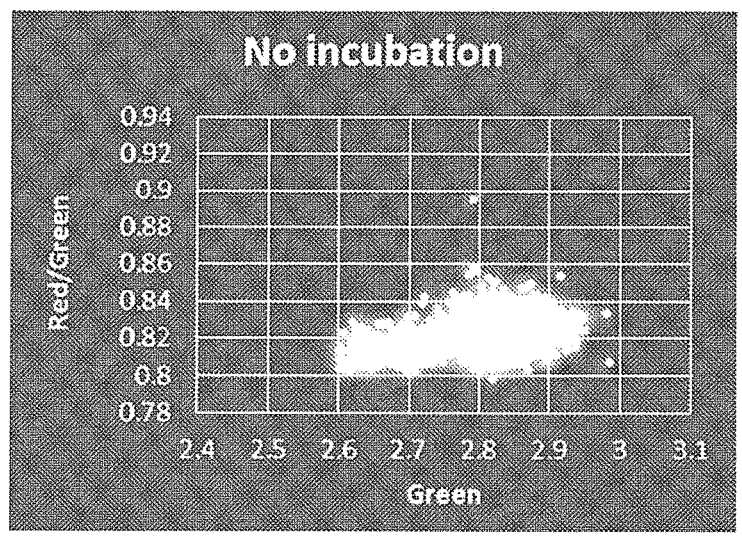
FIGS. 19a-c show detection of single cells in picodroplets using embodiments of the present invention.
Figure 19B:
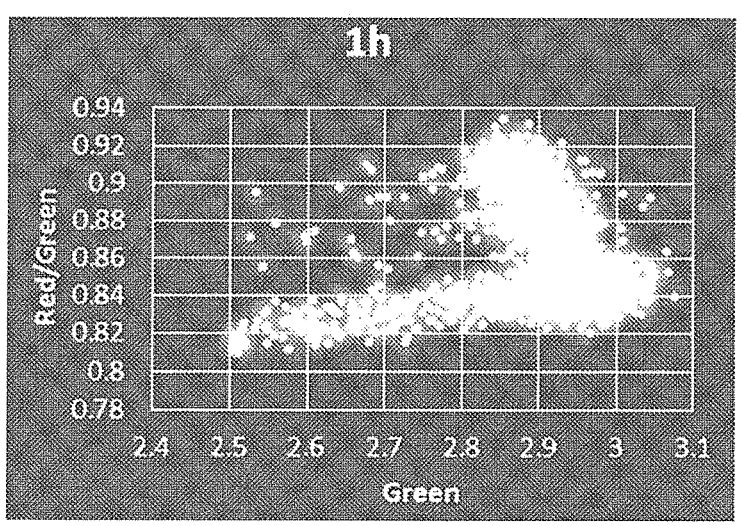
Figure 19C:
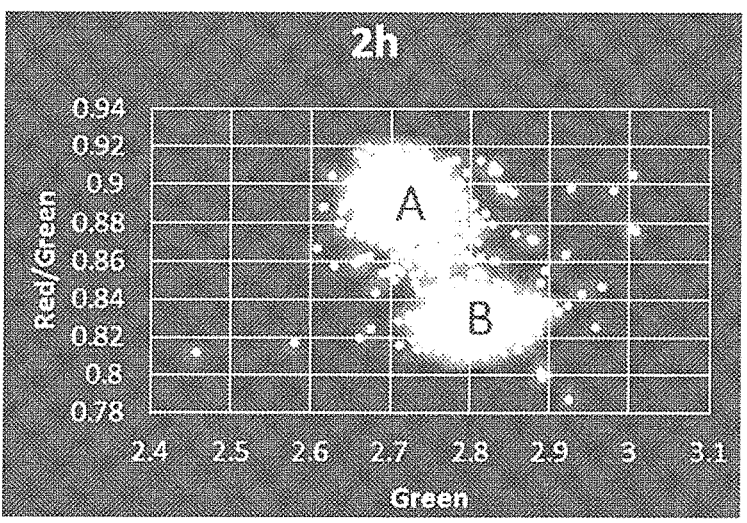

FIGS. 19a-c show detection of single cells in picodroplets using embodiments described herein. In this example, the amount of antibodies produced is determined.

The x-axes of the graphs in FIGS. 19a-c show green fluorescence intensity in arbitrary units, and the y-axes show red/green fluorescence ratio intensity in arbitrary units. The droplets are exposed to green light. In this example, the more antibodies are produced from Chinese Hamster ovary cells, the more the shift from green to red is present in the fluorescence signal as a result of a higher FRET intensity. The skilled person will be familiar with the observation of the green-red shift as a result of a growing number of antibodies. Methods and system described herein show that after 2 h, a significant number of antibodies may be produced from Chinese Hamster ovary cells using embodiments described herein—the cluster labelled "A" shows the population of antibodies. Cluster "B" represents a picodroplet population that contains no cells or no antibodies.

Figure 20A:
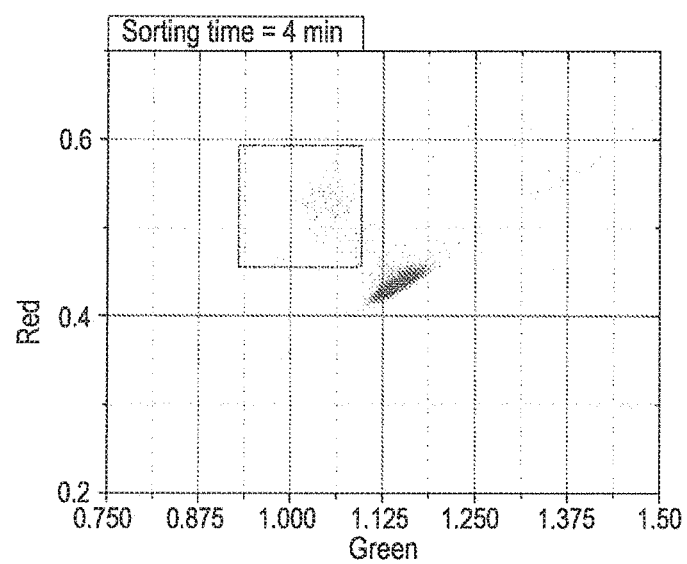
FIGS. 20a-c show time course of scatter plot of red and green fluorescence from picodroplets.
Figure 20B:
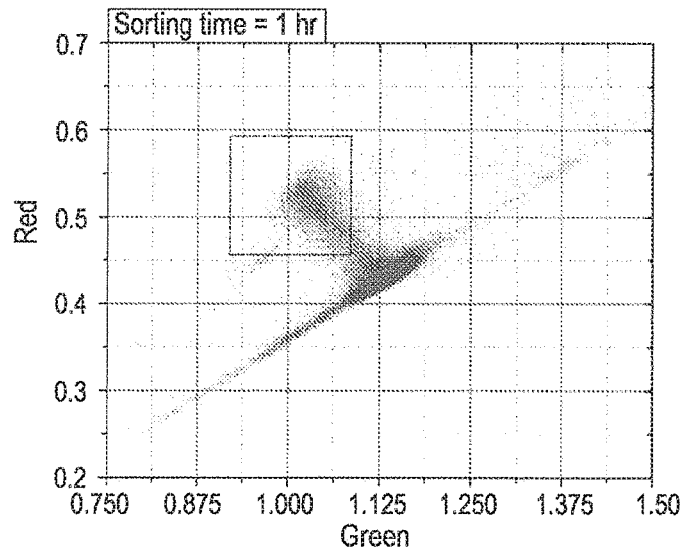
Figure 20C:
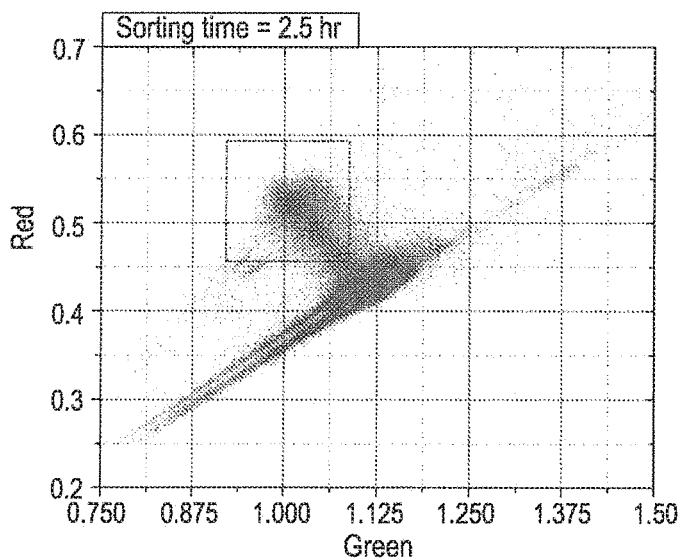

A method may then be implemented to sort only those droplets which exhibit, for example red and green fluorescence intensities which are within certain ranges. This is shown in FIGS. 20a-c which display a time course of scatter plot of red and green fluorescence from picodroplets. The red squares define the gating set for picodroplet sorting, and only those picodroplets which show a red fluorescence within a certain range and a green fluorescence within a certain range may be sorted. It will be appreciated that the shape, size and location of the red square which defines the gating set for picodroplet sorting may be chosen according to specific properties (e.g. fluorescence properties) the droplets (and their entities) should have.

We have described techniques which, in preferred embodiments, are applied to processing droplets of a water-in-oil emulsion containing biological entities. In principle however non-biological entities, such as organic or inorganic materials, may be processed in a similar manner. Likewise the techniques we describe are also in principle applicable to processing droplets of oil in oil-in-water emulsions.

No doubt many other effective alternatives will occur to the skilled person. It will be understood that the invention is not limited to the described embodiments and encompasses modifications apparent to those skilled in the art lying within the spirit and scope of the claims appended hereto.

The invention claimed is:

1. A method of providing a droplet containing one or more entities, the method comprising:
   providing a plurality of entities in a fluid;
   preparing a droplet from said fluid;
   determining whether said droplet contains one or more entities of said plurality of entities, or whether said droplet does not contain a said entity;
   sorting said droplet dependent on an outcome of said determination, wherein said sorting comprises detecting said droplet at a plurality of different sensor locations in a sequence on a path of the droplet along said fluid flow path at different points in time to determine a velocity of said droplet in said fluid flow path for timing said sorting; and
   dispensing said sorted droplet into a reservoir, wherein said dispensing comprises, after said sorting:
   selecting a fluid flow path for fluid containing the sorted droplet; and
   ejecting the sorted droplet from the selected path.

2. The method as claimed in claim 1, wherein said dispensing comprises
   identifying said sorted droplet for dispensing;
   extracting said sorted droplet from a first fluidic flow path of said fluid by transferring said sorted droplet from said first fluidic flow path into a second fluidic flow path; and
   ejecting said sorted droplet from said second fluidic flow path into said reservoir by applying pressure to said second fluidic flow path.

3. The method as claimed in claim 2, wherein said transferring comprises applying pressure to said sorted droplet for dispensing whilst in a portion of said first fluidic flow path and thereafter to transfer said sorted droplet from said first fluidic flow path into a second fluidic flow path and eject said sorted droplet.

4. The method as claimed in claim 1, wherein said dispensing comprises transferring said sorted droplet from said first fluidic flow path into said second fluidic flow path, then applying pressure to said second fluidic flow path to eject the droplet.

5. The method as claimed in claim 1, wherein said dispensing comprises extracting said sorted droplet only when said sorted droplet comprises a defined number of said entities, and/or when said sorted droplet comprises a said entity with a defined property; and optionally wherein a probability of said ejected droplet containing a said single target entity or a said single target combination of said entities is higher than 99.9% based on said preparation, determination, sorting and dispensing.

6. The method as claimed in claim 1, wherein said ejecting comprises ejecting a said sorted droplet at a defined location in response to said determination and/or a property of a said entity.

7. The method as claimed in claim 1, further comprising incubating said droplet for growing and/or maintaining said one or more entities.

8. The method as claimed in claim 2, wherein said transferring of said sorted droplet from said first fluidic flow path into said second fluidic flow path comprises decoupling said sorted droplet from said first fluidic flow path in a decoupler, wherein said decoupler is configured to isolate a said sorted droplet from said first fluidic flow path and to guide a said isolated droplet to said second fluidic flow path.

9. The method as claimed in claim 1, wherein said ejecting comprises heating a fluid in which a said sorted droplet is transported.

10. The method as claimed in claim 1, further comprising injecting a growth media fluid into said second fluidic flow path for ejecting said sorted droplet in said growth media fluid.

11. The method as claimed in claim 1, further comprising:
providing a second plurality of entities in a second fluid;
preparing a second droplet from said second fluid; and
fusing said first droplet prepared from said first fluid and said second droplet prepared from said second fluid to obtain a fused droplet;
wherein said dispensing comprises extracting said fused droplet by transferring said fused droplet from said first fluidic flow path into said second fluidic flow path.

12. The method as claimed in claim 11, wherein said determination and/or sorting are performed prior to said fusion.

13. The method as claimed in claim 11, further comprising:
determining whether said second droplet contains one or more entities of said second plurality of entities, or whether said second droplet does not contain a said entity of said second plurality of entities; and
sorting said second droplet dependent on an outcome of said determination.

14. The method as claimed in claim 13, wherein said fusing is performed only for a said first droplet and a said second droplet which have been determined to contain a said single target entity of said first and second pluralities of entities, respectively, and/or a said first droplet and a said second droplet which have been determined to contain a single target combination of said first and second pluralities of entities, respectively.

15. The method as claimed in claim 11, wherein said fused droplet contains a single pair of two cells, or a single pair of a cell and a reagent, or a single combination of one or more cells, or a single combination of one or more cells with one or more reagents.

16. The method as claimed in claim 1 wherein said one or more entities comprise a biological entity which is a single cell, or a single pair of two cells, or a single pair of a cell and a reagent, the method further comprising metabolising and/or analysing the biological entity contained in said droplet.

17. A method of preparing a droplet containing a single pair of two biological entities, the method comprising:
providing a first plurality of biological entities in a first fluid and providing a second plurality of biological entities in a second fluid;
preparing a first droplet from said first fluid and preparing a second droplet from said second fluid;
determining whether said first droplet contains a single entity of said first plurality of biological entities and whether said second droplet contains a single entity of said second plurality of biological entities; and
fusing said first droplet and said second droplet which have been determined to contain a said single entity, respectively, to form a fused droplet,
wherein the fused droplet contains the single pair of two biological entities, wherein the single pair of two biological entities comprises the single entity previously contained in the first droplet and the single entity previously contained in the second droplet such that the fused droplet allows the single entity previously contained in the first droplet to interact with the single entity previously contained in the second droplet; further comprising
sorting said fused droplet from other droplets, wherein said sorting comprises detecting said droplet at a plurality of different sensor locations in a sequence on a path of the droplet along said fluid flow path; and
dispensing said sorted droplet into a reservoir, wherein said dispensing comprises, after said sorting:
selecting a fluid flow path for fluid containing the sorted droplet; and
ejecting the sorted droplet from the selected path.

18. The method as claimed in claim 17, wherein said fusing is performed by electro-coalescence, by electrically charging one or both of said first and second droplets for fusing said droplets by electrostatic attraction, by physical constriction or physical collision.

19. The method as claimed in claim 17 wherein said single pair of two biological entities comprise a single pair of two cells, or a single pair of a cell and a reagent, the method further comprising metabolising and/or analysing the biological entity contained in said droplet.

* * * * *